US009000183B2

(12) United States Patent
Karlstrom et al.

(10) Patent No.: US 9,000,183 B2
(45) Date of Patent: *Apr. 7, 2015

(54) CYCLOHEXANE-1,2'-INDENE-1',2"-IMIDAZOL COMPOUNDS AND THEIR USE AS BACE INHIBITORS

(71) Applicant: AstraZeneca AB, Sodertalje (SE)

(72) Inventors: Sofia Karlstrom, Cheshire (GB); Peter Soderman, Cheshire (GB); Laszlo Rakos, Cheshire (GB); Liselotte Ohberg, Cheshire (GB); Karin Kolmodin, Cheshire (GB); Lars Sandberg, Cheshire (GB)

(73) Assignee: Astrazeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/916,701

(22) Filed: Jun. 13, 2013

(65) Prior Publication Data

US 2013/0345247 A1 Dec. 26, 2013

Related U.S. Application Data

(60) Provisional application No. 61/661,920, filed on Jun. 20, 2012.

(51) Int. Cl.

| C07D 235/02 | (2006.01) |
|---|---|
| C07D 401/02 | (2006.01) |
| A61K 31/4184 | (2006.01) |
| A61K 31/4439 | (2006.01) |
| A61K 45/06 | (2006.01) |
| C07D 401/04 | (2006.01) |

(52) U.S. Cl.
CPC ............ *C07D 235/02* (2013.01); *C07D 401/02* (2013.01); *A61K 31/4184* (2013.01); *A61K 31/4439* (2013.01); *A61K 45/06* (2013.01); *C07D 401/04* (2013.01)

(58) Field of Classification Search
USPC ..................................................... 548/301.1
See application file for complete search history.

(56) References Cited

U.S. PATENT DOCUMENTS

| 8,415,483 | B2 * | 4/2013 | Csjernyik et al. .......... 548/301.1 |
|---|---|---|---|
| 8,865,911 | B2 * | 10/2014 | Csjernyik et al. .......... 548/301.1 |
| 2013/0210837 | A1 * | 8/2013 | Csjernyik et al. ........ 514/255.05 |
| 2013/0345246 | A1 | 12/2013 | Karlstrom et al. |
| 2013/0345248 | A1 | 12/2013 | Karlstrom et al. |
| 2013/0345272 | A1 | 12/2013 | Karlstrom et al. |
| 2014/0031379 | A1 | 1/2014 | Bohlin et al. |

FOREIGN PATENT DOCUMENTS

| WO | WO2005094822 | 10/2005 |
|---|---|---|
| WO | WO2006138264 | 12/2006 |
| WO | WO2007076247 | 7/2007 |
| WO | WO2007100536 | 9/2007 |
| WO | WO2008076043 | 6/2008 |
| WO | WO2009100169 | 8/2009 |
| WO | WO2010013794 | 2/2010 |
| WO | WO2010021680 | 2/2010 |
| WO | WO2010030954 | 3/2010 |
| WO | WO2010105179 | 9/2010 |
| WO | WO2011002407 | 1/2011 |
| WO | WO2011002408 | 1/2011 |
| WO | WO2011106414 | 9/2011 |
| WO | WO2011123674 | 10/2011 |
| WO | WO2011130741 | 10/2011 |
| WO | WO2012019056 | 2/2012 |
| WO | WO2012040641 | 3/2012 |
| WO | WO2012071458 | 5/2012 |
| WO | WO2012087237 | 6/2012 |

OTHER PUBLICATIONS

Thompson et al., Current Medicinal Chemistry, Oct. 2002, 9(19), pp. 1751-1762.*
Evin et al., "BACE inhibitors as potential therapeutics for Alzheimer's disease," Recent Patents on CNS Drug Discovery, Bentham Science Publishers Ltd, NL, vol. 2, No. 3, Nov. 1, 2007, pp. 188-199.
Hong et al., "Structure of the Protease Domain of Memapsin 2 (β-Secretase) Complexed with Inhibitor," Science 2000, 290, 5489, pp. 150-153.
John et al, "Human β-Secretase (BACE) and BACE Inhibitors," Journal of Medicinal Chemistry, 2003, 46, pp. 4625-4630.
Roberds et al, "BACE knockout mice are healthy despite lacking the primary β-secretase activity in brain: implications for Alzheimer's disease therapeutics," Human Molecular Genetics, 2001, 10, pp. 1317-1324.
Sinha et al, "Purification and cloning of amyloid precursor protein β-secretase from human brain," Nature, 1999, 402, pp. 537-540.

* cited by examiner

*Primary Examiner* — Laura L. Stockton
(74) *Attorney, Agent, or Firm* — Ropes & Gray LLP

(57) ABSTRACT

Cyclohexane-1,2'-indene-1',2"-imidazole compounds, therapeutically acceptable salts thereof, processes for preparation thereof, therapeutic uses of such compounds for treating Aβ-related pathologies such as Down's syndrome, β-amyloid angiopathy, Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration, methods of therapy using such compounds, and pharmaceutical compositions containing such compounds.

18 Claims, No Drawings

CYCLOHEXANE-1,2'-INDENE-1',2"-IMIDAZOL COMPOUNDS AND THEIR USE AS BACE INHIBITORS

CROSS-REFERENCE TO RELATED APPLICATIONS

This application claims the benefit under 35 U.S.C. §119 (e) to U.S. Application Ser. No. 61/661,920 filed on June 20, 2012, which is incorporated herein by reference.

FIELD OF THE INVENTION

The present invention relates to cyclohexane-1,2'-indene-1',2"-imidazole compounds and therapeutically acceptable salts thereof, their pharmaceutical compositions, processes for making them and their use as medicaments for treatment and/or prevention of various diseases. In particular the invention relates to compounds, which are inhibitors of β-secretase and hence inhibit the formation of amyloid β (Aβ) peptides and will be used for treatment and/or prevention of Aβ-related pathologies such as Alzheimer's disease, Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

BACKGROUND

The prime neuropathological event distinguishing Alzheimer's disease (AD) is deposition of the 40-42 residue amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Since soluble Aβ can be found in both plasma and cerebrospinal fluid (CSF), and in the medium from cultured cells, APP has to undergo proteolysis. There are three main cleavages of APP that are relevant to the pathobiology of AD, the so-called α-, β-, and γ-cleavages. The α-cleavage, which occurs roughly in the middle of the Aβ domain in APP is executed by the metalloproteases ADAM10 or ADAM17 (the latter also known as TACE). The β-cleavage, occurring at the N terminus of Aβ, is generated by the transmembrane aspartyl protease Beta site APP Cleaving Enzyme1 (BACE1). The γ-cleavage, generating the Aβ C termini and subsequent release of the peptide, is effected by a multi-subunit aspartyl protease named γ-secretase. ADAM10/17 cleavage followed by γ-secretase cleavage results in the release of the soluble p3 peptide, an N-terminally truncated Aβ fragment that fails to form amyloid deposits in humans. This proteolytic route is commonly referred to as the non-amyloidogenic pathway. Consecutive cleavages by BACE1 and γ-secretase generates the intact Aβ peptide, hence this processing scheme has been termed the amyloidogenic pathway. With this knowledge at hand, it is possible to envision two possible avenues of lowering Aβ production: stimulating non-amyloidogenic processing, or inhibit or modulate amyloidogenic processing. This application focuses on the latter strategy, inhibition or modulation of amyloidogenic processing.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630). β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease or Asp2 or Beta site APP Cleaving Enzyme (BACE), as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-peptide (Aβ).

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof. BACE is therefore an important candidate for the development of drugs as a treatment and/or prophylaxis of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors.

DISCLOSURE OF THE INVENTION

The present invention is directed to compounds according to formula (I):

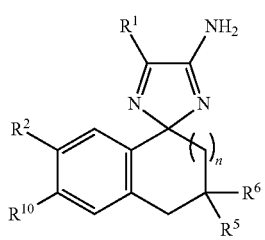

wherein
  n is 0 or 1;
  $R^1$ is $C_{1-6}$alkyl or $C_{1-6}$haloalkyl;
  $R^2$ is hydrogen, $C_{0-6}$alkylaryl, $C_{0-6}$alkylheteroaryl, $C_{2-6}$alkynyl, $C_{2-6}$alkenyl, $C_{1-6}$alkyl, halogen, cyano, $C_{1-6}$haloalkyl, $NHC(O)R^9$ or $OR^8$, wherein said $C_{0-6}$alkylaryl, $C_{0-6}$alkylheteroaryl, $C_{2-6}$alkynyl, $C_{2-6}$alkenyl, $C_{1-6}$alkyl or $C_{1-6}$haloalkyl is optionally substituted with one to three $R^7$;
  $R^5$ and $R^6$ are independently hydrogen, heterocyclyl, $C_{3-6}$cycloalkyl, aryl, heteroaryl or $C_{1-6}$alkyl, wherein said heterocyclyl, $C_{3-6}$cycloalkyl, aryl, heteroaryl or $C_{1-6}$alkyl is optionally substituted with one or two substituents independently selected from halogen, $C_{1-6}$alkyl, $C_{1-6}$haloalkyl, cyano or $OR^8$;
  or $R^5$ and $R^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, $C_{1-6}$alkyl, $C_{1-6}$haloalkyl, cyano, or $OR^8$; and ring B is optionally fused with an aryl or heteroaryl to form a bi- or polycyclic system;
  $R^7$ is independently $C_{1-6}$alkyl, halogen, cyano, $C_{0-6}$alkyl$C_{3-6}$cycloalkyl, $C_{1-6}$haloalkyl, $OC_{1-6}$alkyl, $OC_{1-6}$haloalkyl, $C_{2-6}$alkynyl or $C_{2-6}$alkenyl, wherein said $C_{1-6}$alkyl, $C_{0-6}$alkyl$C_{3-6}$cycloalkyl, $C_{1-6}$haloalkyl, $OC_{1-6}$alkyl, $OC_{1-6}$haloalkyl, $C_{2-6}$alkynyl or $C_{2-6}$alkenyl is optionally substituted with 1-3 substituents independently selected from halogen, cyano, $C_{1-6}$alkyl, $C_{1-6}$haloalkyl, $OC_{1-6}$alkyl, $C_{3-6}$cycloalkyl, $C_{3-6}$halocycloalkyl, and $OC_{1-6}$haloalkyl;
  $R^8$ is independently hydrogen, $C_{1-6}$alkyl, $C_{2-6}$alkynyl, $C_{1-6}$haloalkyl, aryl or heteroaryl, wherein said $C_{1-6}$alkyl, $C_{1-6}$haloalkyl, aryl or heteroaryl is optionally substituted with a group selected from halogen, cyano, $C_{3-6}$cycloalkyl, $C_{3-6}$halocycloalkyl, $OC_{1-6}$alkyl and $C_{1-6}$alkyl;
  $R^9$ is a heteroaryl, wherein said heteroaryl is optionally substituted with halogen, cyano, $OR^8$, $C_{1-6}$haloalkyl or $C_{1-6}$alkyl;
  $R^{10}$ is halogen or methyl;
as a free base or a pharmaceutically acceptable salt thereof.

In one embodiment of the present invention, n is 0.

In one embodiment of the present invention, $R^1$ is $C_{1-3}$alkyl. In another embodiment of the invention, $R^1$ is methyl or ethyl. In yet another embodiment, $R^1$ is methyl.

In one embodiment of the present invention, $R^2$ is aryl, heteroaryl, $C_{2-6}$alkynyl, halogen, $NHC(O)R^9$ or $OR^8$, wherein said aryl, heteroaryl or $C_{2-6}$alkynyl is optionally substituted with one to three $R^7$. In another embodiment of the invention, $R^2$ is aryl, heteroaryl, $C_{2-6}$alkynyl or $OR^8$, wherein said aryl, heteroaryl or $C_{2-6}$alkynyl is optionally substituted with one to three $R^7$.

In one embodiment of the present invention, $R^5$ and $R^6$ are independently hydrogen, $C_{3-6}$cycloalkyl or heterocyclyl wherein said $C_{3-6}$cycloalkyl or heterocyclyl is optionally substituted with one or two substituents independently selected from $C_{1-6}$alkyl or $OR^8$.

In one embodiment of the present invention, $R^5$ and $R^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, $C_{1-6}$alkyl or $OR^8$; and ring B is optionally fused with an aryl or heteroaryl to form a bi- or polycyclic system.

In another embodiment of the invention, $R^5$ and $R^6$ together with the carbon to which they are attached, form a ring B, which is a 3-14 membered cycloalkyl monocyclic ring; and wherein ring B is optionally substituted by one or two substituents independently selected from oxo, halogen, $C_{1-6}$alkyl or $OR^8$. In yet another embodiment, $R^5$ and $R^6$ together with the carbon to which they are attached form a cyclohexyl ring, which is substituted with $OR^8$.

In one embodiment of the present invention, $R^7$ is independently $C_{1-6}$alkyl, halogen, cyano, $C_{0-6}$alkyl$C_{3-6}$cycloalkyl, $C_{1-6}$haloalkyl, $OC_{1-6}$alkyl or $C_{2-6}$alkynyl, wherein said $C_{1-6}$alkyl, $C_{o-6}$alkyl$C_{3-6}$cycloalkyl, $C_{1-6}$haloalkyl, $OC_{1-6}$alkyl, or $C_{2-6}$alkynyl is optionally substituted with 1-3 substituents independently selected from halogen, cyano, $C_{1-6}$alkyl, $C_{1-6}$haloalkyl, $OC_{1-6}$alkyl, $C_{3-6}$cycloalkyl, $C_{3-6}$halocycloalkyl, and $OC_{1-6}$haloalkyl. In another embodiment of the invention, $R^7$ is independently halogen, cyano or $C_{2-6}$alkynyl, wherein said $C_{2-6}$alkynyl is optionally substituted with 1-3 substituents independently selected from $C_{1-6}$alkyl and $C_{1-6}$haloalkyl, $C_{3-6}$cycloalkyl, and $C_{3-6}$halocycloalkyl.

In one embodiment of the present invention, $R^8$ is independently hydrogen, $C_{1-6}$alkyl, or $C_{1-6}$haloalkyl, wherein said $C_{1-6}$alkyl or $C_{1-6}$haloalkyl is optionally substituted with a group selected from halogen, $C_{3-6}$cycloalkyl, $C_{3-6}$halocycloalkyl, $OC_{1-6}$alkyl and $C_{1-6}$alkyl. In another embodiment of the invention, $R^8$ is independently $C_{1-6}$alkyl, or $C_{1-6}$haloalkyl.

In one embodiment of the present invention, $R^9$ is heteroaryl; wherein said heteroaryl is optionally substituted with halogen, cyano, $OR^8$, $C_{1-6}$haloalkyl or $C_{1-6}$alkyl.

In one embodiment of the present invention, $R^{10}$ is halogen. In one embodiment of the present invention, $R^{10}$ is methyl.

In one embodiment of the present invention,
  n is 0 or 1;
  $R^1$ is $C_{1-6}$alkyl;
  $R^2$ is aryl, heteroaryl, $C_{2-6}$alkynyl, halogen, $NHC(O)R^9$ or $OR^8$; wherein said aryl, heteroaryl or $C_{2-6}$alkynyl is optionally substituted with one to three $R^7$;
  $R^5$ and $R^6$ are independently hydrogen, $C_{3-6}$cycloalkyl or heterocyclyl, wherein said $C_{3-6}$cycloalkyl or heterocyclyl, is optionally substituted with one or two substituents independently selected from halogen, $C_{1-6}$alkyl, $C_{1-6}$haloalkyl, cyano or $OR^8$; or $R^5$ and $R^6$ together with the carbon to which they are attached, form a ring B, which is a 3-6 membered cycloalkyl or heterocyclyl monocyclic ring; and wherein ring B is optionally substituted by one or two substituents independently selected from oxo, halogen, $C_{1-6}$alkyl or $OR^8$;
  $R^7$ is independently $C_{1-6}$alkyl, halogen, cyano, $C_{0-6}$alkyl$C_{3-6}$cycloalkyl, $C_{1-6}$haloalkyl, $OC_{1-6}$alkyl or $C_{2-6}$alkynyl, wherein said $C_{1-6}$alkyl, $C_{0-6}$alkyl$C_{3-6}$cycloalkyl, $C_{1-6}$haloalkyl, $OC_{1-6}$alkyl or $C_{2-6}$alkynyl is optionally substituted with 1-3 substituents independently selected from halogen, cyano, $C_{1-6}$alkyl, $C_{1-6}$haloalkyl, $OC_{1-6}$alkyl, $C_{3-6}$cycloalkyl, and $C_{3-6}$halocycloalkyl and $OC_{1-6}$haloalkyl;

$R^8$ is independently $C_{1-6}$alkyl, or $C_{1-6}$haloalkyl; wherein said $C_{1-6}$alkyl or $C_{1-6}$haloalkyl, is optionally substituted with a group selected from halogen, $C_{3-6}$cycloalkyl, $C_{3-6}$halocycloalkyl or $C_{1-6}$alkyl;

$R^9$ is heteroaryl, wherein said heteroaryl is optionally substituted with halogen, cyano, $OR^8$, $C_{1-6}$haloalkyl or $C_{1-6}$alkyl; and $R^{10}$ is halogen or methyl.

In another embodiment of the present invention,
n is 0 or 1;
$R^1$ is $C_{1-3}$alkyl;
$R^2$ is aryl, heteroaryl, $C_{2-6}$alkynyl, halogen, $NHC(O)R^9$ or $OR^8$, wherein said aryl, heteroaryl or $C_{2-6}$alkynyl is optionally substituted with one to three $R^7$;
$R^5$ and $R^6$ are independently hydrogen, $C_{3-6}$cycloalkyl or heterocyclyl, wherein said $C_{3-6}$cycloalkyl or heterocyclyl is optionally substituted with one or two substituents independently selected from $C_{1-6}$alkyl or $OR^8$;
or $R^5$ and $R^6$ together with the carbon to which they are attached, form a ring B, which is a 3-6 membered cycloalkyl or heterocyclyl monocyclic ring; and wherein ring B is optionally substituted by one or two substituents independently selected from oxo, halogen, $C_{1-6}$alkyl or $OR^8$;
$R^7$ is independently $C_{1-6}$alkyl, halogen, cyano, $C_{0-6}$alkyl$C_{3-6}$cycloalkyl, $C_{1-6}$haloalkyl, $OC_{1-6}$alkyl or $C_{2-6}$alkynyl, wherein said $C_{1-6}$alkyl, $C_{0-6}$alkyl$C_{3-6}$cycloalkyl, $C_{1-6}$haloalkyl, $OC_{1-6}$alkyl or $C_{2-6}$alkynyl, is optionally substituted with 1-3 substituents independently selected from halogen, cyano, $C_{1-6}$alkyl, $C_{1-6}$haloalkyl, $OC_{1-6}$alkyl, $C_{3-6}$cycloalkyl, $C_{3-6}$halocycloalkyl and $OC_{1-6}$haloalkyl;

$R^8$ is independently $C_{1-6}$alkyl or $C_{1-6}$haloalkyl; wherein said $C_{1-6}$alkyl or $C_{1-6}$haloalkyl is optionally substituted with a group selected from halogen or $C_{1-6}$alkyl;

$R^9$ is heteroaryl, wherein said heteroaryl is optionally substituted with halogen, cyano, $OR^8$, $C_{1-6}$haloalkyl or $C_{1-6}$alkyl; and $R^{10}$ is halogen or methyl.

In a further embodiment of the present invention,
n is 0;
$R^1$ is methyl or ethyl;
$R^2$ is aryl, heteroaryl, halogen, $OR^8$ or $C_{2-6}$alkynyl, wherein said aryl, heteroaryl or $C_{2-6}$alkynyl is optionally substituted with one to three $R^7$;
$R^5$ and $R^6$ together with the carbon to which they are attached form a cyclohexyl ring, which is substituted with $OR^8$;
$R^7$ is independently $C_{1-3}$alkyl, halogen, cyano or $C_{2-6}$alkynyl;
$R^8$ is $C_{1-6}$alkyl or $C_{1-6}$haloalkyl;
$R^{10}$ is fluoro or methyl.

In yet another embodiment of the present invention,
n is 0;
$R^1$ is methyl or ethyl;
$R^2$ is phenyl or pyridinyl, wherein said phenyl or pyridinyl is optionally substituted with one or two $R^7$;
$R^5$ and $R^6$ together with the carbon to which they are attached form a cyclohexyl ring, which is substituted with methoxy;
$R^7$ is independently chloro, fluoro, cyano or prop-1-yn-1-yl;
$R^{10}$ is fluoro or methyl.

In one embodiment of the present invention,
A is —$CH_2$—;
n is 0;
$R^1$ is methyl or ethyl;
$R^2$ is $OR^8$;
$R^5$ and $R^6$ together with the carbon to which they are attached form a cyclohexyl ring, which is substituted with $OR^8$;
$R^8$ is $C_{1-6}$alkyl or $C_{1-6}$haloalkyl;
$R^{10}$ is fluoro or methyl.

In one embodiment, the compound of formula (I) has the following configuration:

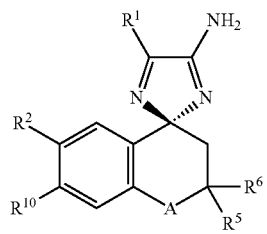

In another embodiment, the invention relates to a compound of formula (I) selected from the group consisting of:
(1r,4r)-6'-Bromo-4-methoxy-5',5"-dimethyl-3'H-dispiro[cyclohexane-1,2'-indene-1',2"-imidazol]-4"-amine;
(1r,4r)-4-Methoxy-5',5"-dimethyl-6'45-(prop-1-yn-1-yl)pyridin-3-yl-3'H-dispiro[cyclohexane-1,2'-indene-1',2"-imidazol]-4"-amine;
3-[(1r,4r)-4"-Amino-4-methoxy-5',5"-dimethyl-3'H-dispiro[cyclohexane-1,2'-indene-1',2"-imidazol]-6'-yl]-5-chlorobenzonitrile;
6'-Bromo-5'-fluoro-4-methoxy-5"-methyl-3'H-dispiro[cyclohexane-1,2'-indene-1',2"-imidazol]-4"-amine;
3-[(1s,4s)-4"-Amino-5'-fluoro-4-methoxy-5"-methyl-3'H-dispiro[cyclohexane-1,2'-indene-1',2"-imidazol]-6'-yl]-5-chlorobenzonitrile;
3-[(1r,1'R,4R)-4"-amino-5'-fluoro-4-methoxy-5"-methyl-3'H-dispiro[cyclohexane-1,2'-indene-1',2"-imidazol]-6'-yl]-5-chlorobenzonitrile (Isomer 1);
3-[(1r,1'S,4S)-4"-amino-5'-fluoro-4-methoxy-5"-methyl-3'H-dispiro[cyclohexane-1,2'-indene-1',2"-imidazol]-6'-yl]-5-chlorobenzonitrile (Isomer 2);
(1r,4r)-6'-(5-Chloropyridin-3-yl)-5'-fluoro-4-methoxy-5"-methyl-3'H-dispiro[cyclohexane-1,2'-indene-1',2"-imidazol]-4"-amine;
3-[(1r,4r)-4"-Amino-5'-fluoro-4-methoxy-5"-methyl-3'H-dispiro[cyclohexane-1,2'-indene-1',2"-imidazol]-6'-yl]-5-fluorobenzonitrile;
3-[(1r,1'R,4R)-4"-amino-5'-fluoro-4-methoxy-5"-methyl-3'H-dispiro[cyclohexane-1,2'-indene-1',2"-imidazol]-6'-yl]-5-fluorobenzonitrile (Isomer 1);
3-[(1r,1'S,4S)-4"-amino-5'-fluoro-4-methoxy-5"-methyl-3'H-dispiro[cyclohexane-1,2'-indene-1',2"-imidazol]-6'-yl]-5-fluorobenzonitrile (Isomer 2); and
5'-Fluoro-6'-(3-fluoropropoxy)-4-methoxy-5"-methyl-3'H-dispiro[cyclohexane-1,2'-indene-1',2"-imidazol]-4"-amine
or a pharmaceutically acceptable salt of any foregoing compound.

In yet another embodiment, the invention relates to a compound of formula (I), or a pharmaceutically acceptable salt thereof, with the proviso that any of the specific Examples are individually disclaimed.

The present invention relates to the use of compounds of formula (I) as hereinbefore defined as well as to the salts thereof. Salts for use in pharmaceutical compositions will be pharmaceutically acceptable salts, but other salts may be useful in the production of the compounds of formula (I).

The compounds of the formula (I) may be administered in the form of a prodrug which is broken down in the human or animal body to give a compound of the formula (I). Examples of prodrugs include in vivo hydrolysable esters of a compound of the formula (I). An in vivo hydrolysable (or cleavable) ester of a compound of the formula (I) that contains a carboxy or a hydroxy group is, for example, a pharmaceutically acceptable ester which is hydrolysed in the human or animal body to produce the parent acid or alcohol. Various forms of prodrugs are known in the art.

The definitions set forth in this application are intended to clarify terms used throughout this application. The term "herein" means the entire application.

A variety of compounds in the present invention may exist in particular geometric or stereoisomeric forms. The present invention takes into account all such compounds, including tautomers, cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used in this application, the term "optionally substituted" means that substitution is optional and therefore it is possible for the designated atom or moiety to be unsubstituted.

As used herein, "alkyl", used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{0-6}$alkyl" denotes alkyl having 0, 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. In the case where a subscript is the integer 0 (zero) the group to which the subscript refers to indicates that the group may be absent, i.e. there is a direct bond between the groups.

As used herein, "alkenyl" used alone or as a suffix or prefix is intended to include both branched and straight-chain alkene or olefin containing aliphatic hydrocarbon groups having from 2 to 12 carbon atoms or if a specified number of carbon atoms is provided then that specific number would be intended. For example "$C_{2-6}$alkenyl" denotes alkenyl having 2, 3, 4, 5 or 6 carbon atoms. Examples of alkenyl include, but are not limited to, vinyl, allyl, 1-propenyl, 1-butenyl, 2-butenyl, 3-butenyl, 2-methylbut-2-enyl, 3-methylbut-1-enyl, 1-pentenyl, 3-pentenyl and 4-hexenyl.

As used herein, "alkynyl" used alone or as a suffix or prefix is intended to include to include both branched and straight-chain alkynyl or olefin containing aliphatic hydrocarbon groups having from 2 to 12 carbon atoms or if a specified number of carbon atoms is provided then that specific number would be intended. For example ethynyl, propynyl (e.g. 1-propynyl, 2-propynyl), 3-butynyl, pentynyl, hexynyl and 1-methylpent-2-ynyl.

As used herein, "aromatic" refers to hydrocarbonyl groups having one or more unsaturated carbon ring(s) having aromatic characters, (e.g. 4n+2 delocalized electrons) and comprising up to 14 carbon atoms. In addition "heteroaromatic" refers to groups having one or more unsaturated rings containing carbon and one or more heteroatoms such as nitrogen, oxygen or sulfur having aromatic character (e.g. 4n+2 delocalized electrons).

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. Examples of polycyclic rings include, but are not limited to, 2,3-dihydro-1,4-benzodioxine and 2,3-dihydro-1-benzofuran.

As used herein, the terms "cycloalkyl" or "carbocyclyl" are intended to include saturated ring groups, having the specified number of carbon atoms. These may include fused or bridged polycyclic systems. Cycloalkyls have from 3 to 14 carbon atoms in their ring structure. In one embodiment, cycloalkyls have 3, 4, 5, or 6 carbons in the ring structure. For example, "$C_{3-6}$cycloalkyl" denotes such groups as cyclopropyl, cyclobutyl, cyclopentyl, or cyclohexyl.

As used herein, the term "cycloalkenyl" is intended to include unsaturated ring groups, having the specified number of carbon atoms. These may include fused or bridged polycyclic systems. Cycloalkenyls may have from 3 to 10 carbon atoms in their ring structure. In one embodiment, cycloalkenyls have 3, 4, 5, or 6 carbons in the ring structure. For example, "$C_{3-6}$cycloalkenyl" denotes such groups as cyclopropenyl, cyclobutenyl, cyclopentenyl, or cyclohexenyl.

As used herein, "halo" or "halogen" refers to fluoro, chloro, bromo, and iodo.

"Counterion" is used to represent a small, negatively or positively charged species such as chloride, bromide, hydroxide, acetate, sulfate, tosylate, benezensulfonate, ammonium, lithium ion and sodium ion and the like.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, which may, unless otherwise specified, be carbon or nitrogen linked, wherein a —$CH_2$— group is optionally be replaced by a —C(O)—; and where unless stated to the contrary a ring nitrogen or sulphur atom is optionally oxidised to form the N-oxide or S-oxide(s) or a ring nitrogen is optionally quarternized; wherein a ring —NH is optionally substituted with acetyl, formyl, methyl or mesyl; and a ring is optionally substituted with one or more halo. It is understood that when the total number of S and O atoms in the heterocyclyl exceeds 1, then these heteroatoms are not adjacent to one another. If the said heterocyclyl group is bi- or tricyclic then at least one of the rings may optionally be a heteroaromatic or aromatic ring provided that at least one of the rings is non-heteroaromatic. If the said heterocyclyl group is monocyclic then it must not be aromatic. Examples of heterocyclyls include, but are not limited to, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, tetrahydropyranyl, dihydro-2H-pyranyl, tetrahydrofuranyl, tetrahydro-thiopyranyl, tetrahydro-thiopyran 1-oxide, tetrahydro-thiopyran 1,1-dioxide, 1H-pyridin-2-one, and 2,5-dioxoimidazolidinyl.

As used herein, "heteroaryl" refers to a heteroaromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, benzoxazolyl, aza-benzoxazolyl imidazothiazolyl, benzo[1,4]dioxinyl, benzo[1,3]dioxolyl and the like. In some embodiments, the heteroaryl group has from 1 to 20 carbon atoms, and in further embodiments from 3 to 20 carbon atoms. In some embodiments, the heteroaryl group contains 3 to 14, 4 to 14, 3 to 7, or 5 to 6 ring-forming atoms. In some embodiments, the heteroaryl group has 1 to 4, 1 to 3, or 1 to 2 heteroatoms. In some embodiments, the heteroaryl group has 1 heteroatom.

As used herein, "haloalkyl", used alone or as a suffix or prefix, is intended to include both branched and straight chain saturated aliphatic hydrocarbon groups, having at least one halogen substituent and having from 1 to 12 carbon atoms or if a specified number of carbon atoms is provided then that specific number would be intended. For example "$C_{0-6}$haloalkyl" denotes alkyl having 0, 1, 2, 3, 4, 5 or 6 carbon atoms. Examples of haloalkyl include, but are not limited to, fluoromethyl, difluoromethyl, trifluoromethyl, chlorofluoromethyl, 1-fluoroethyl, 3-fluoropropyl, 2-chloropropyl, 3,4-difluorobutyl.

As used herein, the phrase "protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been reviewed (Greene, T. W.; Wuts, P. G. M. *Protective Groups in Organic Synthesis*, $3^{rd}$ ed.; Wiley: New York, 1999).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

The present invention further includes all tautomeric forms of compounds of the invention. As used herein, "tautomer" means other structural isomers that exist in equilibrium resulting from the migration of a hydrogen atom. For example, keto-enol tautomerism where the resulting compound has the properties of both a ketone and an unsaturated alcohol. Other examples of tautomerism include 2H-imidazole-4-amine and its tautomer 1,2-dihydroimidazol-5-imine, and 2 H-imidazol-4-thiol and its tautomer 1,2-dihydroimidazol-5-thione. It is understood that in compound representations throughout this description, only one of the possible tautomers of the compound is drawn or named.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labeled compounds of the invention. An "isotopically" or "radiolabeled" compound is a compound of the invention where one or more atoms are replaced or substituted by an atom having an atomic mass or mass number different from the atomic mass or mass number typically found in nature (i.e., naturally occurring). Suitable isotopes that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{78}Br$, $^{76}Br$, $^{77}Br$, $^{123}I$, $^{124}I$, $^{125}I$ and $^{131}I$. The radionucleotide that is incorporated in the instant radio-labelled compounds will depend on the specific application of that radio-labelled compound. For example, for in vitro receptor labelling and competition assays, compounds that incorporate $^{3}H$, $^{14}C$, $^{82}Br$, $^{125}I$, $^{131}I$ or $^{35}S$ will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^3$H, $^{15}$C, $^{125}$I, $^{35}$S and $^{82}$Br.

Compounds of the present invention may be administered orally, by parenteral, buccal, vaginal, rectal, inhalation, or insufflation administration, sublingually, intramuscularly, subcutaneously, topically, intranasally, intraperitoneally, intrathoracically, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

In another aspect, the invention relates to a compound of formula (I), or a pharmaceutically acceptable salt thereof, for use as a medicament, e.g. for treatment or prevention of Aβ-related pathologies.

In another aspect, the invention relates to the use of a compound of formula (I), or a pharmaceutically acceptable salt thereof, in the manufacture of a medicament for treatment or prevention of Aβ-related pathologies.

In another aspect, the invention relates to a method of treating or preventing Aβ-related pathologies in a mammal, such as a human being, comprising administering to a mammal in need thereof a therapeutically effective amount of a compound of Formula (I), or a pharmaceutically acceptable salt thereof.

The compounds of the invention, and their pharmaceutically acceptable salts, thereby provide methods of treatment of Aβ-related pathologies, such as, but not limited to, Alzheimer's disease, Down's syndrome, β-amyloid angiopathy, cerebral amyloid angiopathy, hereditary cerebral hemorrhage, a disorder associated with cognitive impairment, MCI ("mild cognitive impairment"), memory loss, attention deficit symptoms associated with Alzheimer's disease, neurodegeneration associated with Alzheimer's disease, dementia of mixed vascular origin, dementia of degenerative origin, presenile dementia, senile dementia, dementia associated with Parkinson's disease, progressive supranuclear palsy traumatic brain injury and cortical basal degeneration.

In another aspect, the invention relates to a pharmaceutical composition comprising as active ingredient a therapeutically effective amount of a compound of formula (I), or a pharmaceutically acceptable salt thereof, in association with at least one pharmaceutically acceptable excipient, carrier or diluent.

In another aspect, the invention relates to a method of inhibiting activity of BACE with a compound according to formula (I).

In another aspect, the invention relates to a method of treating or preventing an Aβ-related pathology in a mammal, such as a human being, comprising administering to said patient a therapeutically effective amount of a compound according to formula (I), or a pharmaceutically acceptable salt thereof, and at least one cognitive enhancing agent, memory enhancing agent, or cholinesterase inhibitor, wherein said Aβ-related pathology is Alzheimer's disease.

In another aspect, the invention relates to a pharmaceutical composition comprising (i) a compound of formula (I), or a pharmaceutically acceptable salt thereof, (ii) an additional therapeutic agent, or a pharmaceutically acceptable salt thereof, and (iii) pharmaceutically acceptable excipients, carriers or diluents.

In another aspect, the invention relates to a pharmaceutical composition comprising (i) a compound of formula (I), or a pharmaceutically acceptable salt thereof, (ii) at least one agent selected from the group consisting of cognitive enhancing agents, memory enhancing agents and cholinesterase inhibitors, and (iii) pharmaceutically acceptable excipients, carriers or diluents.

The treatment of Aβ-related pathology defined herein may be applied as a mono therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (ARICEPT), galantamine (REMINYL or RAZADYNE), rivastigmine (EXELON), tacrine (COGNEX) and memantine (NAMENDA, AXURA or EBIXA). Atypical antipsychotic agents includes, but not limited to, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON) and olanzapine/fluoxetine (marketed as SYMBYAX).

Such conjoint treatment may be achieved by way of the simultaneous, sequential or separate dosing of the individual components of the treatment. Such combination products employ the compounds of the invention.

Additional conventional chemotherapy may include one or more of the following categories of agents: (i) antidepressants, (ii) atypical antipsychotics, (iii) antipsychotics, (iv) anxiolytics, (v) anticonvulsants, (vi) currently used Alzheimer's therapies, (vii) Parkinson's therapies, (viii) migraine therapies, (ix) stroke therapies, (x) urinary incontinence therapies, (xi) neuropathic pain therapies, (xii) nociceptive pain therapies, (xiii) insomnia therapies and (xiv) mood stabilizers. Known treatments for the foregoing therapies may be employed in combination with the invention described herein.

Such combination products employ the compounds of this invention within the dosage range described herein and the other pharmaceutically active compound or compounds within approved dosage ranges and/or the dosage described in the publication reference.

Preparation of Compounds

The compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3rd Edition, Wiley-Interscience, New York, 1999. It is understood that MWs (MW) can alternatively be used for the heating of reaction mixtures. Another aspect of the present invention provides a process for preparing a compound of formula (I), or a pharmaceutically acceptable salt thereof, wherein, unless specified otherwise, $R^1$-$R^{10}$, n and A are defined as for formula (I) above, or are groups that can be converted into $R^1$-$R^{10}$, or A in subsequent transformations. A compound of formula (Ia) may be equivalent to a compound of formula (I). LG represents a leaving group such as halogen (such as chlorine, bromine or iodine) or an alkyl-, aryl- or haloalkyl-sulfonate (such as triflate) and PG represents a protecting group. Said process comprises of:

Method (i): Formation of a Corresponding Compound of Formula (IIIa):

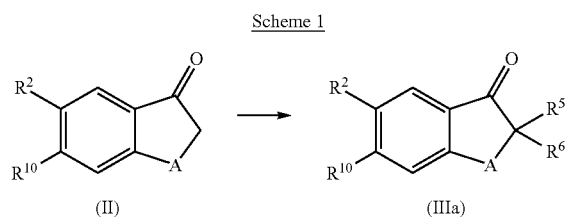

Scheme 1

(II)     (IIIa)

A ketone of formula (II), is treated with a suitable base such as sodium hydride, KOtBu, or LDA in presence of a suitable electrophile such as methyl acrylate, (bis-substituted) alkyl halide, triflate or mesylate to give a compound of formula (IIIa) (Scheme 1). Said reaction may be performed at a temperature range between 0° C. and +90° C., in a suitable solvent, such as tetrahydrofuran, 2-Me THF or dimethylformamide. Alkyations could be carried out in a sequential way with intermediates isolated and purified or in a one-pot stepwise fashion. If the reactions yield a product substituted with a ester, olefin, cyano, sulfone or the like, it could optionally be reacted further by Dieckman cyclization, RCM, nucleophilic substitution or cycloaddition. The resulting spirocyclic ring may optionally contain one or more substituent which may be further converted by known functional group transformations, such as decarboxylation, reduction of a ketone to an alcohol and conversion of said alcohol to an ether.

Method (ii): Formation of a Corresponding Compound of Formula (IIIa):

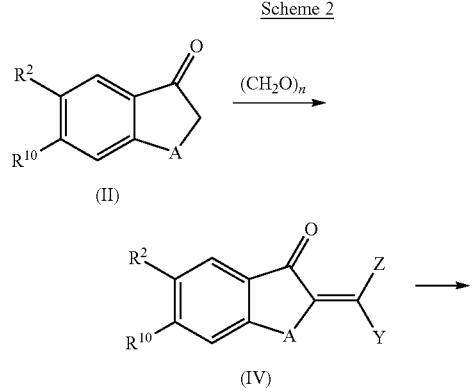

Scheme 2

(II)

(IV)

(IIIa)

A ketone of formula (II), is reacted with an aldehyde or ketone such as formaldehyde in a temperature range between room temperature and +100° C. in presence of N-Methyla-nilinium trifluoroacetate, in a suitable solvent such THF, benzene or toluene (Scheme 2). The intermediate (IV), wherein Z and Y are defined as for example hydrogen or alkyl, can be reacted with various dienes such as (buta-1,3-dien-2-yloxy)trimethylsilane utilizing the Diels-Alder reaction in a temperature range between 0° C. and +90° C. optionally in a sealed tube. The reaction can be carried out neat or in a suitable solvent such as DCM, benzene, toluene, THF or 2-Me THF. A Lewis acid or any other agents that may assist the reaction can be added to yield enriched enantiomers or diastereomers. The resulting spirocyclic ring may optionally contain one or more substituent which may be further converted by known functional group transformations, such as decarboxylation, reduction of a ketone to an alcohol and conversion of said alcohol to an ether.

Method (iii) Formation of a Corresponding Compound of Formula (VII):

Scheme 3

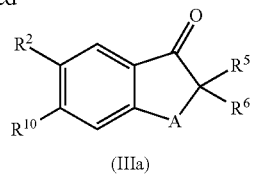

(V)

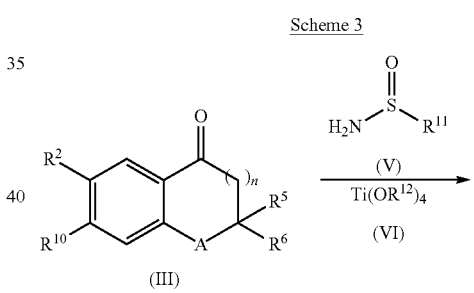

(III)     $\xrightarrow{Ti(OR^{12})_4}$     (VI)

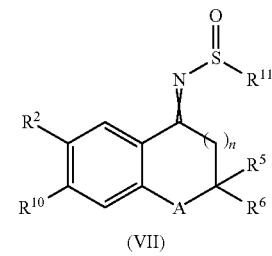

(VII)

A compound of formula (VII) may be obtained by reacting a compound of formula (III) with a compound of formula (V) (Scheme 3), wherein $R^{11}$ is alkyl (such as for example tert-butyl). The reaction is performed in the presence of a suitable Lewis acid, such as a compound of formula (VI), wherein $R^{12}$ is alkyl (such as ethyl or isopropyl). The reaction is performed in a suitable solvent to (such as DCM, 2-methyl-tetrahydrofuran or tetrahydrofuran) at a temperature between room temperature and reflux temperature, optionally with azeotropic distillation to remove an alcohol formed in the reaction.

15
Method (iv) Formation of a Corresponding Compound of Formula (X):

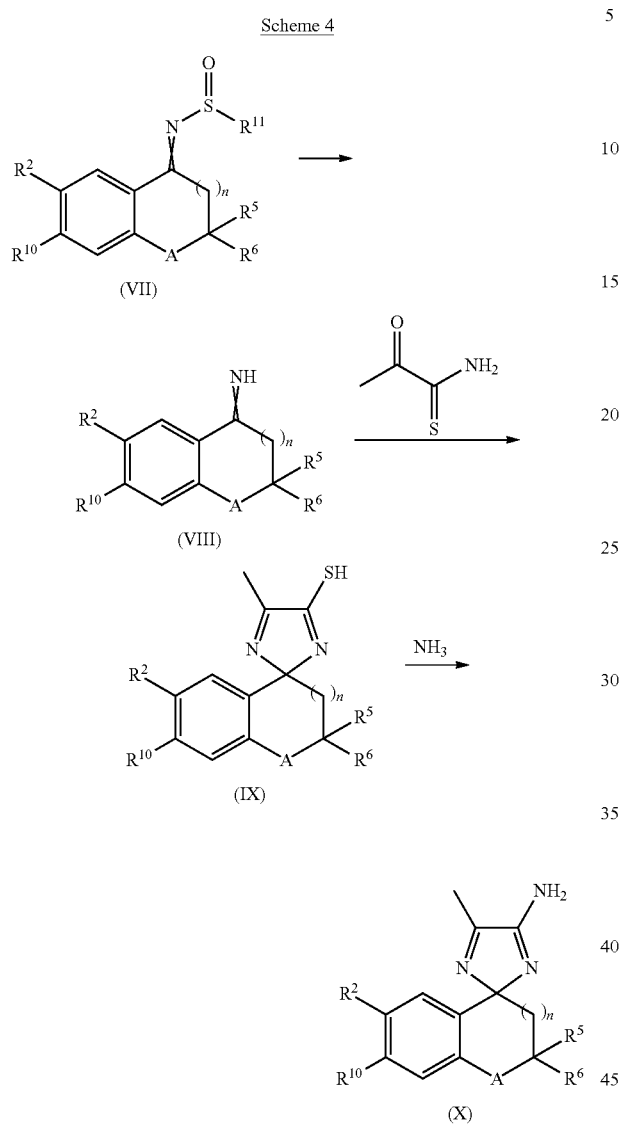

16
Method (v) Formation of a Corresponding Compound of Formula (I):

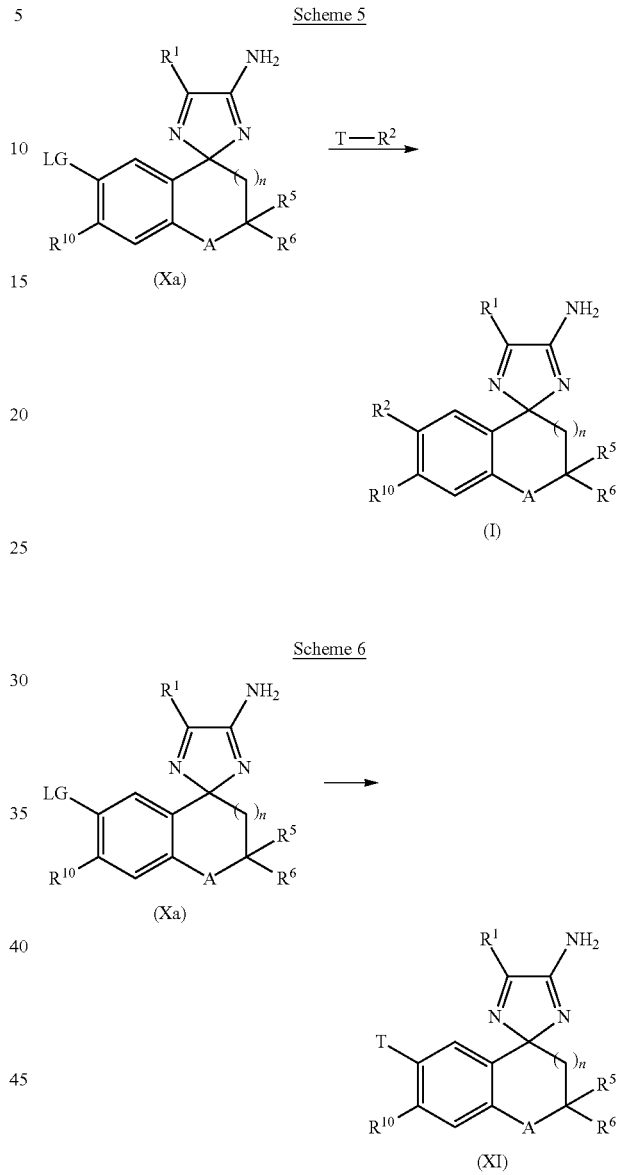

A compound of formula (VIII) may be obtained by reacting a compound (VII) (wherein $R^{11}$ is alkyl (such as for example tert-butyl as in method (iii), formula VII), using a suitable method of removing the sulfonamide protecting group to form imine (VIII) (Scheme 4). A suitable method may be, but is not limited to, treating said compound VII with an acid such as hydrochloric acid under dry conditions in a suitable solvent (such as dioxane or tetrahydrofuran). Compound (VIII) may be isolated or reacted further without isolation. A compound of formula (VIII) is further reacted with 2-oxopropane thioamide (described in Asinger et al. *Justus Liebigs Annalen der Chemie* 1971, vol 744, p. 51-64) optionally in the presence of triethyl orthoformate, in a solvent such as methanol at a temperature between room temperature and reflux temperature, optionally under Dean-Stark conditions, to yield a compound of formula (IX). The transformation to a compound of formula (X) may be performed by reacting the intermediate of formula (IX) with ammonia.

A compound of formula (I) wherein $R^2$ is an optionally substituted aryl or heteroaryl, may be obtained (Scheme 5) by starting from, for example, a compound of formula (Xa), wherein LG is a leaving group such as a halide (for example bromo), and reacting said compound of formula (Xa) with a boronic acid or a boronic ester or a stannane of formula T-$R^2$, wherein T is for example $B(OH)_2$, $B(Oalkyl)_2$, or $SnR_3$, and $R^2$ is an optionally substituted aryl or a heteroaryl, in the presence of a transition metal catalyst such as a palladium catalyst, such as [1,1'-bis(diphenylphosphino)ferrocene]palladium(II) chloride, tetrakis(triphenylphosphine)-palladium (0), palladium diphenylphosphineferrocene dichloride, palladium(II) acetate or bis(dibenzylideneacetone) palladium (0), or sodium tetrachloropalladate (II). Optionally, a suitable ligand such as triphenylphosphine, tri-tert-butylphosphine or 2-(dicyclohexylphosphino)biphenyl, 3-(di-tert-butylphosphonium)propane sulfonate, or zinc and sodium triphenylphosphinetrimetasulfonate, is used. A suitable base, such as cesium fluoride, an alkyl amine, such as triethyl amine, or an alkali metal or alkaline earth metal carbonate or hydroxide such as potassium carbonate, sodium carbonate, cesium carbonate, or sodium hydroxide, may be used in the reaction. Said reaction may be performed in a suitable solvent, such as toluene, tetrahydrofuran, 2-methyl-tetrahydrofuran, dioxane, dimethoxyethane, water, ethanol, N,N-dimethylacetamide, acetonitrile or N,N-dimethylformamide, or mixtures thereof.

Alternatively a compound of formula (I) wherein $R^2$ is an optionally substituted aryl or heteroaryl can be prepared from compound (Xa) by transformation into a compound (XI) wherein T is as described above ($B(OH)_2$ or $B(Oalkyl)_2$) (Scheme 6). Compound (XI) is then reacted with a compound $R^2$-LG wherein $R^2$ is an optionally substituted aryl or heteroaryl and LG is a leaving group such as a halogen to yield compound (1).

Method (vi) Formation of a Corresponding Compound of Formula (I):

A compound of formula (I), wherein $R^2$ is cyano, may be obtained (Scheme 5) by starting from, for example, a compound of formula (Xa), wherein LG is a leaving group such as a halogen, (such as iodide, bromide or chlorine), and reacting said compound of formula (Xa) with a metal cyano reagent such as copper(I) cyanide.

Method (vii) Formation of a Corresponding Compound of Formula (I):

A compound of formula (I), wherein $R^2$ is an alkyl group such as methyl may be generated from a compound of formula (Xa) (Scheme 5), wherein LG represents a leaving group, such as a halogen, (such as iodide, bromide or chlorine), by reaction with an organometallic reagent generated from zinc iodide and methylmagnesium bromide under the influence of a transition metal catalyst such as for example bis(triphenylphosphine)palladium(II) chloride.

Method (viii) Formation of a Corresponding Compound of Formula (I):

A compound of formula (I), wherein $R^2$ is an alkyne may be generated from a compound of formula (Xa) (Scheme 5), wherein LG represents a leaving group, such as a halogen, (such as iodide or bromide), by reaction with an alkyne such as an alkylethyne or a cycloalkylethyne under the influence of a transition metal catalyst such as for example tetrakis(triphenylphosphine)palladium(0) in presence of a base such as triethylamine and copper(I)iodide. The alkyne is optionally silylated. Said reaction may be performed at a temperature range between room temperature and reflux temperature, in a suitable solvent, such as THF or toluene.

Method (ix) Formation of a Corresponding Compound of Formula (I):

A compound of formula (I) wherein $R^2$ is $NHC(O)R^9$ may be prepared according to Scheme 5 by reacting a compound of formula (Xa) with a compound $R^9C(O)NH_2$ in the presence of a suitable palladium catalyst such as palladium(II) acetate, optionally in the presence of a suitable ligand such as Xantphos. Said reaction is preformed in the presence of a suitable base such as cesium carbonate in a suitable solvent such as THF or 2-methyl-tetrahydrofuran at a temperature between reflux temperature and 160° C.

Method (x) Formation of a Corresponding Compound of Formula (I):

A compound of formula (I) wherein $R^2$ is $NHC(O)R^9$ may be obtained from a compound of formula (Xa) as shown in Scheme 7.

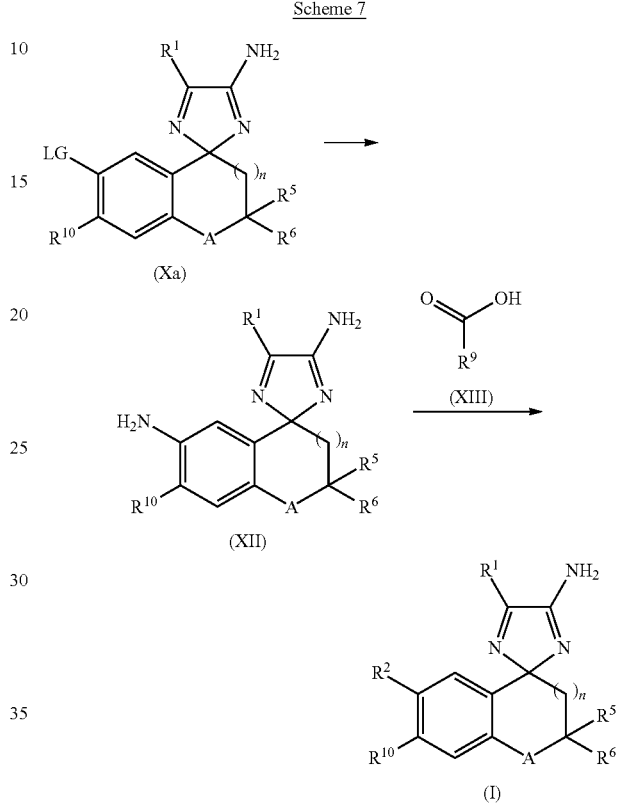

A compound of formula (Xa) is reacted with ammonia in the presence of trans-4-hydroxy-L-proline, potassium carbonate and copper(I)iodide in a solvent such as DMSO at a temperature between room temperature and 150° C. to give a compound of formula (XII). Said compound of formula (XII) is further reacted with a carboxylic acid of formula (XIII) wherein $R^9$ is as defined above. The reaction is performed in the presence of a suitable amide coupling agent such as 1-(3-dimethylaminopropyl)-3-ethyl-carbodiimide in a solvent such as DMF, optionally in the presence of hydrochloric acid.

Method (xi) Formation of a Compound of Formula (I)

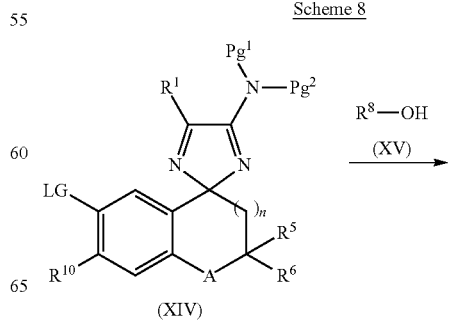

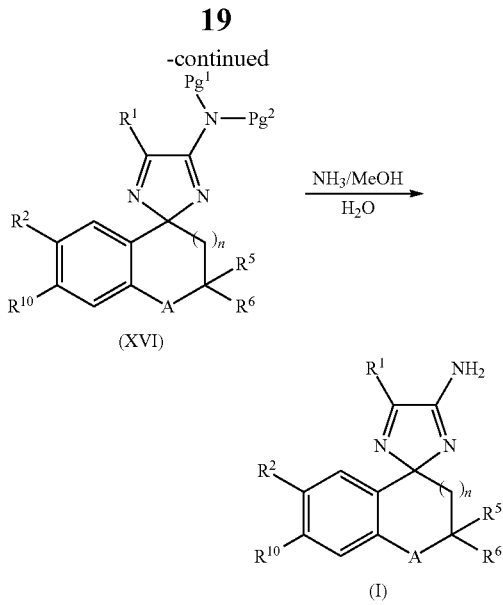

A compound of formula (XVI) wherein $R^2$ is $OR^8$ may be prepared by reacting a compound of formula (XIV), wherein LG represents a leaving group, such as a halogen, (such as iodide or bromide), $Pg^1$ and $Pg^2$ represents hydrogen and/or a suitable protecting group such as tert-butoxycarbonyl, with an alcohol of formula (XV) in the presence of a suitable palladium catalyst such as palladium(II) acetate, optionally in the presence of a suitable ligand such as di-tert-butyl(2',4',6'-triisopropyl-3-methoxy-6-methylbiphenyl-2-yl)phosphine (Scheme 8). Said reaction is performed in the presence of a suitable base such as cesium carbonate in a suitable solvent such as THF, 2-methyl-tetrahydrofuran or toluene at a temperature between 20° C. and 160° C. The compound of formula (I) may be obtained from compound of formula (XVI) wherein $Pg^1$ and/or $Pg^2$ is tert-butoxycarbonyl, by reacting with a solution of $NH_3$, such as in methanol, in the presence of water, at a temperature between 60° C. and 100° C.

Compounds of formula (II), (V), (VI), (XIII), (XV), T-$R^2$, are commercially available compounds, or are known in the literature, or they are prepared by standard processes known in the art.

General Methods:

All solvents used were of analytical grade and commercially available anhydrous solvents were routinely used for reactions. Starting materials used were available from commercial sources, or prepared according to literature procedures. Room temperature refers to 20-25° C. Solvent mixture compositions are given as volume percentages or volume ratios.

MW heating was performed in a Biotage Creator, Initiator or Smith Synthesizer Single-mode MW cavity producing continuous irradiation at 2450 MHz. It is understood that MWs can be used for the heating of reaction mixtures.

Thin layer chromatography (TLC) was performed on Merck TLC-plates (Silica gel 60 $F_{254}$) and spots were UV visualized. Straight phase flash column chromatography ("flash chromatography") was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.

NMR:

NMR spectra were recorded on a 400-600 MHz NMR spectrometer fitted with a probe of suitable configuration. Spectra were recorded at ambient temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, $CD_3OD$ δ 3.30, acetone-$d_6$ 2.04 or $CDCl_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.

HPLC, HPLCMS, and LCMS Analyses:

High pressure liquid chromatography (HPLC) was performed on a reversed phase (RP) column. A linear gradient was applied using for example mobile phase A (10 mM $NH_4OAc$ in 5% $CH_3OH$ or 5% $CH_3CN$ (aq.), or 0.1% $NH_3$ (aq.) or 0.1% formic acid (aq.)) and B ($CH_3OH$ or $CH_3CN$). Mass spectrometry (MS) analyses were performed in positive and/or negative ion mode using electrospray ionization (ESI+/−) and/or atmospheric pressure chemical ionization (APCI+/−).

GCFID and GCMS Analyses:

Gas chromatography (GC) was performed on a GC equipped with a mass spectrometer (MS) or a flame ionization detector (FID). The MS ion source was either an electron impact (EI) or a chemical ionization (CI, reactant gas methane). For separation a capillary column was used for example DB-5MS, (J&W Scientific). A linear temperature gradient was applied.

Preparative Chromatography:

Preparative chromatography was run on a Waters Fraction-Lynx system with a Autosampler combined Automated Fraction Collector (Waters 2767), Gradient Pump (Waters 2525), Column Switch (Waters CFO) and PDA (Waters 2996). Column; XBridge® Prep C8 10 μm OBD™ 19×300 mm, with guard column; XTerra® Prep MS C8 10 μm 19×10 mm Cartridge. A gradient of A (95% 0.1 M $NH_4OAc$ in MilliQ water and 5% MeCN) in B (100% MeCN) or a gradient of A (95% 0.1 M $NH_4OAc$ in MilliQ water and 5% MeOH), A (0.2% $NH_3$ in MilliQ water) or A (0.2% formic acid in MilliQ water) in B (100% MeOH) was applied for LC-separation at flow rate 20 ml/min. Preparative chiral chromatography for separation of isomers was run on for example an LaPrep® system using the specified column and mobile phase system.

SFC Analyses:

Supercritical Fluid Chromatography (SFC) was performed on a straight phase column. A isocratic flow was applied using mobile phase A ($CO_2$) and for example mobile phase B (MeOH, EtOH or IPA).

Straight Phase HPLC Analyses:

High pressure liquid chromatography (HPLC) was performed on a straight phase column. A linear gradient or isocratic flow was applied using for example mobile phase A (Heptane) and B (EtOH or IPA).

High-Resolution Mass Spectrometry (HRMS)

For accurate mass, measurements were performed on a Waters Synapt-G2 mass spectrometer equipped with a Lock-Spray source and connected to an Acquity UPLC system with a PDA detector and an Acquity UPLC BEH C 18 column. The measured mass confirmed the elemental composition within 3 ppm.

Abbreviations

ACN acetonitrile
aq aqueous
Atm atmospheric pressure

Boc t-butoxycarbonyl
Borax di-sodium tetraborate or sodium borate or sodium tetraborate
Cbz benzyloxycarbonyl
CDI 1,1'-carbonyldiimidazole
dba dibenzylideneacetone
DCM DCM
DEA diethylamine
DIBAL-H diisobutylaluminium hydride
DIPEA diisopropylethylamine
DMAP 4-Dimethylaminopyridine
DME 1,2-dimethoxyethane
DMF N,N-dimethyl formamide
DMSO dimethyl sulfoxide
dppf 1,1'-bis(diphenylphosphino)ferrocene
Et$_2$O diethyl ether
EtOAc ethyl acetate
EtOH ethanol
eq. or equiv. equivalent
h hour(s)
HPLC high performance liquid chromatography
IPA isopropanol
LCMS liquid chromatography mass spectrometry
LiHMDS lithium bis(trimethylsilyl)amide
MeOH methanol
min minute(s)
MS mass spectrometry
MW MW(s)
NH$_4$OAc ammonium acetate
NMR nuclear magnetic resonance
ox oxidation
Psi pounds per square inch
quant. quantitative
RCM ring closing metathesis
r.t. room temperature
sat. saturated
SFC supercritical fluid chromatography
TFA trifluoroacetic acid
THF tetrahydrofuran
TLC thin layer chromatography
TMEDA tetramethylethylenediamine
UPLC ultra performance liquid chromatography
2-Me THF 2-methyl tetrahydrofuran Compounds have been named using CambridgeSoft MedChem ELN v2.2 or ACD/Name, version 10.0, or 10.06, or version 12.01, software from Advanced Chemistry Development, Inc. (ACD/Labs), Toronto ON, Canada, www.acdlabs.com, or Lexichem, version 1.9, software from OpenEye.

INTERMEDIATES

Intermediate 1

2-Oxopropanethioamide

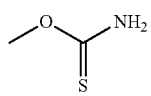

To a −10° C. solution of THF (1700 mL) and acetyl cyanide (250 mL, 3.15 mol) was H$_2$S bubbled for approx 45 min. The bubbling was stopped, and the solution was stirred until the temp. was −10° C. More H$_2$S was bubbled until the temperature was stable at −10° C. Triethylamine (2.2 mL, 15.8 mmol) in THF (20 mL) was added dropwise (very exothermic reaction). at such rate that temp. was kept between 0° C. and −3° C. After addition was completed, the temp. was set to +4° C. and the mixture was stirred overnight. Nitrogen was flushed through the reaction for 30 min and the mixture was concentrated to give the title product (319 g, 98% yield). $^1$H NMR (500 MHz, CDCl$_3$) δ ppm 2.67 (s, 3 H), 7.30-7.81 (m, 1 H), 7.97-8.52 (m, 1 H); $^{13}$C NMR (126 MHz, CDCl$_3$) δ ppm 25.1, 190.8, 192.5; MS (ES+) m/z 104 [M+H]$^+$.

Intermediate 2

6'-Bromo-5'-methylspiro[cyclohexane-1,2'-indene]-1',4(3'H)-dione

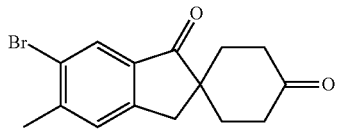

To a mixture of 6-bromo-5-methyl-2,3-dihydro-1H-inden-1-one (commercially available), 1.45 g, 6.42 mmol) and methyl acrylate (1.28 mL, 14.1 mmol) in 2-Me THF (6 mL) cooled to 0° C. was added potassium tert-butoxide (0.864 g, 7.70 mmol) in portions. After stirring for 2 h at r.t., water (9.0 mL) and potassium hydroxide (0.36 g, 6.42 mmol) were added and the mixture was heated at reflux overnight. The mixture was allowed to cool to r.t. and brine was added. The layers were separated and the aqueous layer was extracted with DCM. The combined organic layers were dried over Na$_2$SO$_4$, filtered and evaporated to yield 1.38 g (70% yield) of the title compound: $^1$H NMR (500 MHz, CDCl$_3$) δ ppm 1.86 (m, 2 H) 2.20 (m, 2 H) 2.45 (m, 2 H) 2.51 (s, 3 H) 2.71 (dt, 2 H) 3.13 (s, 2 H) 7.38 (s, 1 H) 7.95 (m, 1 H): MS (ES+) m/z 307, 309 [M+H]$^+$.

Intermediate 3

6'-Bromo-4-hydroxy-5'-methylspiro[cyclohexane-1,2'-inden]-1'(3'H)-one

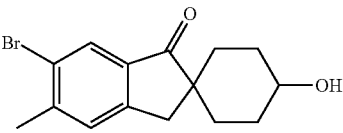 [SMILES: Cc1cc2c(cc1Br)C(=O)C1(CCC(O)CC1)C2]

6'-Bromo-5'-methylspiro[cyclohexane-1,2'-indene]-1',4 (3'H)-dione (Intermediate 2, 1.38 g, 4.49 mmol) and propan-2-ol (16.6 mL, 215 mmol) were heated to 75° C. Ground NaOH (0.176 g, 4.40 mmol) was added. The resulting mixture was heated at reflux for 1.5 h and was then allowed to cool to r.t. The mixture was concentrated to half the volume and then water (15 mL) and toluene (15 mL) were added together with 6 M aq. HCl (0.749 mL, 4.49 mmol). The layers were separated and the aqueous layer was re-extracted with toluene (15 mL). The combined organic layers were dried over Na$_2$SO$_4$, concentrated and dried in vacuo to afford 1.36 g (98% yield) of the title compound as a mixture of isomers (~70:30 mixture of isomers with the hydroxyl group in equa-

Intermediate 4

6'-Bromo-4-methoxy-5'-methylspiro[cyclohexane-1, 2'-inden]-1'(3'H)-one

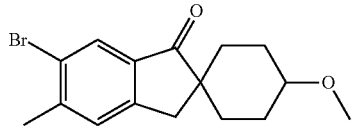 [SMILES: COC1CCC2(CC1)Cc1cc(C)c(Br)cc1C2=O]

6'-Bromo-4-hydroxy-5'-methylspiro[cyclohexane-1,2'-inden]-1'(3'H)-one (Intermediate 3, 1.72 g, 5.57 mmol) was dissolved in 2-Me THF (13 mL) under an inert atmosphere and the solution was cooled to 0° C. Methyl iodide (0.453 mL, 7.24 mmol) was added followed by portionwise addition of potassium tert-butoxide (0.875 g, 7.80 mmol). The resulting mixture was stirred at r.t. for 1 h. Potassium tert-butoxide (0.250 g, 2.23 mmol) was added and stirring continued. After another 30 min, potassium tert-butoxide (0.094 g, 0.84 mmol) was added and stirring continued. After a total of 4 h, full conversion was obtained and water (6 mL) and brine (3 mL) were added. The phases were separated and the organic layer was treated with charcoal and diatomaceous earth and then filtered through a plug of diatomaceous earth. The plug was rinsed with EtOAc and the organics were concentrated to yield 1.3 g (77% yield) of the title compound as a mixture of isomers with the methoxy group in either equatorial position (major) or axial position (minor). This mixture was used in the next step without further purification: MS (ES+) m/z 323, 325 [M+H]$^+$.

Intermediate 5

6-Bromo-5-fluoro-2-methylene-2,3-dihydro-1H-inden-1-one

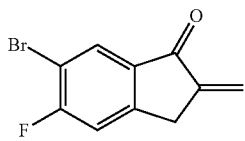

6-Bromo-5-fluoro-2,3-dihydro-1H-inden-1-one (commercially available), 4 g, 17.5 mmol), paraformaldehyde (2.48 g, 78.6 mmol) and N-methylanilinium trifluoroacetate (5.79 g, 26.2 mmol) were dissolved in anhydrous THF (80 mL) and refluxed overnight. The mixture was cooled to r.t. and concentrated. The residue was re-dissolved in EtOAc and brine. The phases were separated and the organic phase was dried over sodium sulfate and concentrated. The product was purified by flash column chromatography using heptane/EtOAc 7:1 as eluent affording the title compound (2.99 g, 71% yield).

$^1$H NMR (400 MHz, CDCl$_3$) δ ppm 3.73 (s, 3 H) 5.69 (m, 1 H) 6.39 (m, 1 H) 7.25 (s, 2 H) 8.10 (d, 1 H); MS (EI) m/z 240, 242 M$^+$.

Intermediate 6

6'-Bromo-5'-fluorospiro[cyclohexane-1,2'-indene]-1', 4(3'H)-dione

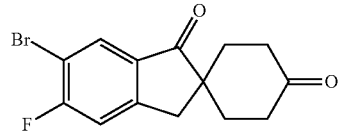

To a cold (0° C.) solution of (buta-1,3-dien-2-yloxy)trimethylsilane (1.86 mL, 10.6 mmol) in DCM (80 mL) was 6-bromo-5-fluoro-2-methylene-2,3-dihydro-1H-inden-1-one (Intermediate 5, 2.32 g, 9.62 mmol) added. Boron trifluoride diethyl etherate (0.594 mL, 4.81 mmol) was added at 0° C. The reaction was stirred for 30 min., and then quenched with MeOH (1.0 mL). The reaction mixture was acidified with aq. 2 M HCl solution, and extracted with DCM. The organic phase was washed with brine, dried over sodium sulfate and concentrated. The product was purified by flash column chromatography using a stepwise gradient of heptane/EtOAc (7:1-3.5:1-1:1), to give the title compound (1.60 g, 53% yield). $^1$H NMR (500 MHz, CDCl$_3$) δ ppm 1.83-1.94 (m, 2 H) 2.17-2.27 (m, 2 H) 2.38-2.51 (m, 2 H) 2.72 (dt, 2 H) 3.18 (s, 2 H) 7.25 (d, 1 H) 8.01 (d, 1 H); MS (ES+) m/z 311,313 [M+H]$^+$.

Intermediate 7

6'-Bromo-5'-fluoro-4-hydroxyspiro[cyclohexane-1, 2'-inden]-1'(3'H)-one

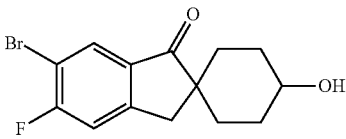 [SMILES: O=C1c2cc(Br)c(F)cc2CC12CCC(O)CC2]

To a solution of 6'-bromo-5'-fluorospiro[cyclohexane-1,2'-indene]-1',4(3'H)-dione (Intermediate 6, 2.0 g, 6.43 mmol) in DCM (15 mL), was borane tert-butylamine complex (0.212 g, 2.44 mmol) added at 0° C. After 1 h, conc HCl (1.5 mL) was added, followed by 20% aq. NaCl (20 mL). The mixture was allowed to reach r.t. and was stirred for 30 min. The phases were separated and the water phase was charged with DCM. The organic phases were combined, concentrated and dried in vacuo to give the title compound (1.94 g, 96% yield) as a diasteromer mixture in the ratio ~4:1 (established by HPLC and NMR analysis). The compound was used in the next step. MS (ES+) m/z 313, 315 [M+H]$^+$; $^1$H NMR (500 MHz, CDCl$_3$, signals for both isomers) δ ppm 1.29-1.37 (m, 0.7 H) 1.37-1.53 (m, 4.7 H) 1.69-1.77 (m, 0.8 H) 1.77-1.86 (m, 2 H) 1.91-2.00 (m, 0.7 H) 2.04-2.14 (m, 2.7 H) 2.97 (s, 0.5 H) 3.00

(s, 2 H) 3.77 (s, 1 H) 4.01-4.07 (m, 0.25 H) 7.17-7.20 (d, 0.30 H) 7.22 (d, 1 H) 7.98 (d, 1.2 H).

Intermediate 8

6'-Bromo-5'-fluoro-4-methoxyspiro[cyclohexane-1,2'-inden]-1'(3'H)-one

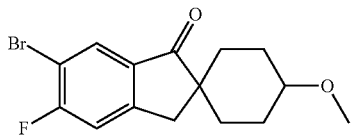

A solution of 6'-bromo-5'-fluoro-4-hydroxyspiro[cyclohexane-1,2'-inden]-1'(3'H)-one (Intermediate 7, 1.94 g, 6.19 mmol) and methyl iodide (9.65 ml, 154 mmol) in 2-Me THF (80 mL) was heated to 35° C. Potassium tert-pentoxide (1.7 M in toluene) (5.01 g, 9.91 mmol) was slowly added dropwise over 10 min and the resulting mixture was stirred at 35° C. for 1 h. The reaction mixture was cooled to r.t., and partitioned between water and EtOAC. The organic phase was dried over magnesium sulfate and concentrated, to give the title compound (2.0 g, 99% yield). The product was used in the next step. MS (EI) m/z 326, 328 M+.

Intermediate 9

N-(5'-Bromo-4-methoxy-6'-methylspiro[cyclohexane-1,2'-indene]-3'(1'H)-ylidene)-2-methylpropane-2-sulfinamide

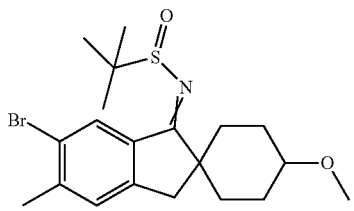

6'-Bromo-4-methoxy-5'-methylspiro[cyclohexane-1,2'-inden]-1'(3'H)-one (Intermediate 4, 1.38 g, 4.27 mmol) and 2-methylpropane-2-sulfinamide (0.931 g, 7.68 mmol) were dissolved in 2-Me THF (8 mL). Titanium(IV) ethoxide (1.78 mL, 8.53 mmol) was added and the resulting mixture was heated to reflux overnight. 2-Methylpropane-2-sulfinamide (0.259 g, 2.13 mmol) and titanium(IV) ethoxide (0.624 mL, 2.99 mmol) were added and heating was continued. After a total of 4 days, the reaction was allowed to cool to r.t. and diluted with EtOAc (25 mL). Water (12 mL) was added dropwise under vigorous stirring and after stirring for another 10 min, the mixture was allowed to stand without stirring for 1.5 h. The solids were filtered off and the solvent was evaporated. The residue was purified by flash chromatography using a gradient of 0-30% EtOAc in heptane as eluent to afford 812 mg (45% yield) of the title compound: $^1$H NMR (500 MHz, DMSO-$d_6$) δ ppm 1.23 (m, 9 H), 1.31 (m, 2 H), 1.58 (m, 4 H), 1.90 (m, 1 H), 2.02 (m, 1 H), 2.42 (s, 3 H), 2.98 (m, 2 H), 3.18 (m, 1 H), 3.25 (m, 3 H), 7.51 (m, 1 H), 8.53 (m, 1 H); MS (ES+) m/z 426, 428 [M+H]+.

Intermediate 10

6'-Bromo-4-methoxy-5'-methylspiro[cyclohexane-1,2'-inden]-1'(3'H)-imine

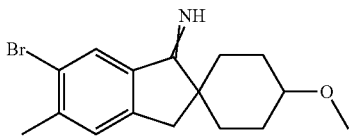

HCl-solution (4 M in 1,4-dioxane, 4.76 mL, 19.0 mmol) was added to a solution of N-(5'-bromo-4-methoxy-6'-methylspiro[cyclohexane-1,2'-indene]-3'(1'H)-ylidene)-2-methylpropane-2-sulfinamide (Intermediate 9, 812 mg, 1.90 mmol) in anhydrous 1,4-dioxane (8 mL). The resulting mixture was stirred under a nitrogen atmosphere at r.t. for 1 h. The mixture was concentrated and the residue was dissolved in a small amount of DCM (~4-6 mL). Et$_2$O (14 mL) was added and the solid was filtered off and washed with Et$_2$O. The solid was partitioned between DCM (10 mL) and saturated aqueous NaHCO$_3$ (8 mL). The phases were separated and the organic layer concentrated. The product (446 mg) was used directly in the next step: MS (EI) m/z 321, 323 [M+.].

Intermediate 11

(1r,4r)-6'-Bromo-4-methoxy-5',5"-dimethyl-3'H-dispiro[cyclohexane-1,2'-indene-1',2"-imidazole]-4"(3"H)-thione

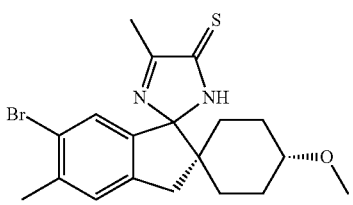

6'-Bromo-4-methoxy-5'-methylspiro[cyclohexane-1,2'-inden]-1'(3'H)-imine (Intermediate 10, 446 mg, 1.38 mmol) and 2-oxopropanethioamide (Intermediate 1, 428 mg, 4.15 mmol) were dissolved in dry MeOH (10 mL) and the resulting orange solution was heated at 60° C. under N$_2$ (g) overnight. After 16 h, the reaction was allowed to cool to r.t. and the mixture was concentrated. The product was purified by flash chromatography using a gradient of 0-50% EtOAc in heptane as eluent to yield 171 mg (30% yield) of the title compound: $^1$H NMR (500 MHz, DMSO-$d_6$) δ ppm 1.10 (d, 1 H), 1.21 (m, 3 H), 1.48 (m, 2 H), 1.87 (m, 2 H), 2.26 (s, 3 H), 2.34 (s, 3 H), 3.00 (m, 3 H), 3.20 (s, 3 H), 6.98 (s, 1 H), 7.36 (s, 1 H), 12.33 (s, 1 H); MS (ES+) m/z 407, 409 [M+H]+.

Intermediate 12

N-(5'-Bromo-6'-fluoro-4-methoxyspiro[cyclohexane-1,2'-indene]-3'(1'H)-ylidene)-2-methylpropane-2-sulfinamide

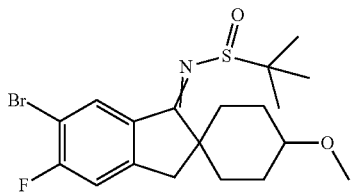

6'-Bromo-5'-fluoro-4-methoxyspiro[cyclohexane-1,2'-inden]-1'(3'H)-one (Intermediate 8, 2.0 g, 6.11 mmol), 2-methylpropane-2-sulfinamide (1.11 g, 9.17 mmol) and titanium ethoxide (2.52 mL, 12.2 mmol) were dissolved in 2-Me THF (31 mL) and heated to reflux for 48 h. The reaction was allowed to cool to r.t. whereafter it was diluted with EtOAc (75 mL). Water (25 mL) was added dropwise over 10 min under vigorous stirring and then the mixture was left standing without stirring for 1.5 h. The solids were filtered off and the organics were concentrated. The was purified by silica gel chromatography using a stepwise gradient of heptane/EtOAC (5:1-4:1-3:1-1:1), to give the title compound (1.5 g, 57% yield) as a diasteromer mixture in the ratio ~4:1 (established by HPLC and NMR analysis) (1.50 g, 57% yield). The was used in the next step. $^1$H NMR (500 MHz, CDCl$_3$, signals for both isomers) δ ppm 1.20-1.29 (m, 1 H) 1.30-1.41 (m, 14 H) 1.50-1.60 (m, 4 H) 1.60-1.68 (m, 1 H) 1.97-2.08 (m, 1 H) 2.08-2.20 (m, 2.5 H) 2.24-2.32 (m, 0.3 H) 2.95-3.02 (m, 2.5 H) 3.22-3.32 (m, 1 H) 3.35 (s, 0.9 H) 3.40 (s, 3 H) 3.48-3.53 (m, 0.3 H) 7.09-7.11 (m, 0.3 H) 7.13 (d, 1 H) 8.64-8.88 (m, 1 H); MS (ES+) m/z 430, 432 [M+H]+.

Intermediate 13

6'-Bromo-5'-fluoro-4-methoxyspiro[cyclohexane-1,2'-inden]-1'(3'H)-imine

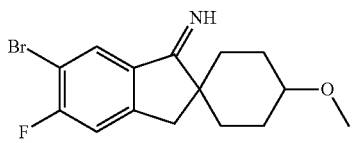

HCl (4 M in 1,4-dioxane) (7.84 mL, 31.4 mmol) was added to a solution of N-(5'-bromo-6'-fluoro-4-methoxyspiro[cyclohexane-1,2'-indene]-3'(1'H)-ylidene)-2-methylpropane-2-sulfinamide (Intermediate 12, 1.35 g, 3.14 mmol) in anhydrous 1,4-dioxane (23 mL) and the resulting mixture was stirred under an argon atmosphere for 15 min. Et$_2$O (60 mL) was added and the precipitate was filtered off and washed with Et$_2$O, then partitioned between DCM and saturated aqueous NaHCO$_3$. The phases were separated, the organic phase dried over sodium sulfate and concentrated to give the title compound (0.95 g, 93% yield) that was used without further purification. MS (ES+) m/z 326, 328 [M+H]+.

Intermediate 14

(1r,4r)-6'-Bromo-5'-fluoro-4-methoxy-5''-methyl-3'H-dispiro[cyclohexane-1,2'-indene-1',2''-imidazole]-4''(3''H)-thione

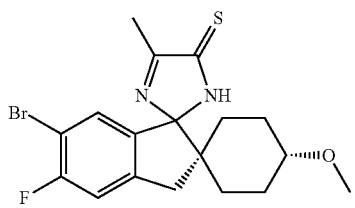

(1r,4r)-6'-Bromo-5'-fluoro-4-methoxyspiro[cyclohexane-1,2'-inden]-1'(3'H)-imine (Intermediate 13, 0.95 g, 2.91 mmol) and trimethyl orthoformate (0.319 mL, 2.91 mmol) dissolved in 2-propanol (40 mL) was heated to 80° C. 2-Oxopropanethioamide (Intermediate 1, 0.52 g, 4.99 mmol) was added and the reaction was stirred 80° C. overnight. More 2-oxopropanethioamide (0.15 g, 1.46 mmol) was added and the reaction was heated for another 1 h. The mixture was concentrated and the residue was purified by silica gel chromatography using heptane/EtOAC (5:1-4:1) as eluent to give the title compound (0.502 g, 42% yield). MS (ES+) m/z 411, 413 [M+H]+.

Intermediate 15

Di-tert-butyl (6'-bromo-5'-fluoro-4-methoxy-5''-methyl-3'H-dispiro[cyclohexane-1,2'-indene-1',2''-imidazol]-4''-yl)imidodicarbonate

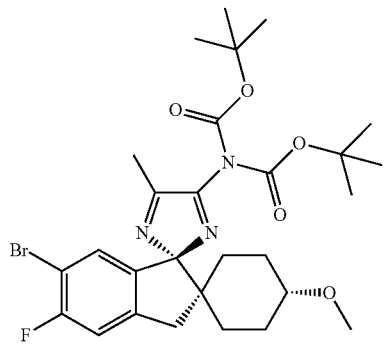 [SMILES: CO[C@H]1CC[C@]2(CC1)Cc1cc(F)c(Br)cc1[C@]21N=C(C)C(N(C(=O)OC(C)(C)C)C(=O)OC(C)(C)C)=N1]

Di-tert-butyl dicarbonate (0.411 g, 1.89 mmol), triethylamine (0.275 mL, 1.98 mmol) and DMAP (11 mg, 0.09 mmol) were added to a solution of 6'-bromo-5'-fluoro-4-methoxy-5''-methyl-3'H-dispiro[cyclohexane-1,2'-indene-1',2''-imidazol]-4''-amine (Example 4, 0.354 g, 0.90 mmol) in DCM (8 mL). The resulting mixture was stirred at r.t overnight. The reaction mixture was diluted with DCM and washed with aq. 2 M HCl solution, water, sat. aq. NaHCO$_3$ and brine. The organic layer was dried over MgSO$_4$, filtered, and concentrated under vacuum to give the title compound (0.50 g, 93% yield) that was used in the next step. MS (ES+) m/z 438,440 [M+H]+ (observed mass is fragment without C(CH3) and OC(O)C(CH3).

Intermediate 16

Di-tert-butyl [5'-fluoro-6'-(3-fluoropropoxy)-4-methoxy-5"-methyl-3'H-dispiro[cyclohexane-1,2'-indene-1',2"-imidazol]-4"-yl]imidodicarbonat

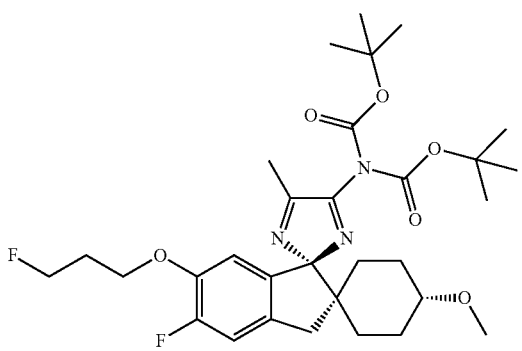 [SMILES: CO[C@H]1CC[C@]2(CC1)Cc1cc(F)c(OCCCF)cc1[C@]21N=C(C)C(N(C(=O)OC(C)(C)C)C(=O)OC(C)(C)C)=N1]

Di-tert-butyl (6'-bromo-5'-fluoro-4-methoxy-5"-methyl-3'H-dispiro[cyclohexane-1,2'-indene-1',2"-imidazol]-4"-yl)imidodicarbonate (Intermediate 15, 0.261 g, 0.44 mmol), di-tert-butyl(2',4',6'-triisopropyl-3-methoxy-6-methylbiphenyl-2-yl)phosphine (0.012 g, 0.03 mmol), cesium carbonate (0.053 mL, 0.66 mmol), allylpalladium chloride dimer (3.1 mg, 8.78 μmol) and 3-fluoropropan-1-ol (0.069 g, 0.88 mmol) were placed in a tube. The tube was capped and inerted by vacuum-nitrogen purge cycles. Toluene (3 mL) was added and the mixture was heated at 90° C. o.n. More 3-fluoropropan-1-ol (0.069 g, 0.88 mmol) was added, and the reaction was heated for another 3 h. The mixture was allowed to cool to r.t. and was then filtered and concentrated. The product was used directly in the next step.

EXAMPLES

Example 1

(1r,4r)-6'-Bromo-4-methoxy-5',5"-dimethyl-3'H-dispiro[cyclohexane-1,2'-indene-1',2"-imidazol]-4"-amine

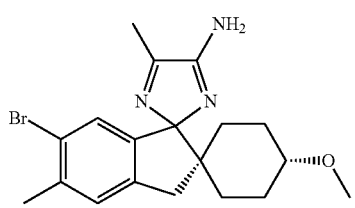

(1r,4r)-6'-Bromo-4-methoxy-5',5"-dimethyl-3'H-dispiro[cyclohexane-1,2'-indene-1',2"-imidazole]-4"(3"H)-thione (Intermediate 11, 0.170 g, 0.42 mmol) and ammonia (7 M in MeOH, 2.5 mL, 17.5 mmol) were mixed in a MW vial. The vial was sealed and the reaction was heated at 120° C. for 30 min in a MW reactor. The mixture was concentrated and the residue was dissolved in ammonia (7 M in MeOH, 2.5 mL, 17.5 mmol) and heated once more at 120° C. for 30 min in a MW reactor. This cycle was repeated three more times (5 runs in total). After evaporation of the solvent, the residue was partitioned between DCM (15 mL) and 2 M citric acid (10 mL). The phases were separated and the organic layer was extracted with 2 M citric acid (10 mL). The organic layer was discarded while the combined aqueous phases were basified to pH 12 by addition of 50% aq. NaOH and extracted with EtOAc (2×20 mL). The combined organic layers were treated with charcoal and filtered through diatomaceous earth. The diatomaceous earth was rinsed with EtOAc and the organic phase was concentrated, yielding the title compound (121 mg, 74% yield): $^1$H NMR (500 MHz, DMSO-$d_6$) δ ppm 0.91 (d, 1 H), 1.14 (d, 2 H), 1.40 (m, 3 H), 1.81 (m, 2 H), 2.15 (s, 3 H), 2.30 (s, 3 H), 2.92 (m, 3 H), 3.18 (s, 3 H), 6.56 (s, 2 H), 6.66 (s, 1 H), 7.27 (s, 1 H); MS (APCI+) m/z 390 [M+H]+.

Example 2

(1r,4r)-4-Methoxy-5',5"-dimethyl-6'-[5-(prop-1-yn-1-yl)pyridin-3-yl]-3'H-dispiro[cyclohexane-1,2'-indene-1',2"-imidazol]-4"-amine

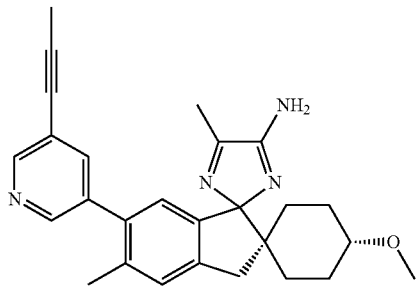

Sodium tetrachloropalladate(II) (1.5 mg, 5.12 μmol), 3-(di-tert-butylphosphonium)propane sulfonate (2.8 mg, 10.3 μmol), (1r,4r)-6'-bromo-4-methoxy-5',5"-dimethyl-3'H-dispiro[cyclohexane-1,2'-indene-1',2"-imidazol]-4"-amine (Example 1, 40 mg, 0.10 mmol) and 5-(prop-1-ynyl)pyridin-3-ylboronic acid (21.5 mg, 0.13 mmol), were added to a vial. 2-Me THF (1 mL) and 2 M aq. potassium carbonate (0.154 mL, 0.31 mmol) were added and the mixture was iii degassed by bubbling $N_2$ (g). The vial was sealed and heated in a MW reactor at 90° C. for 30 min. Water (5 mL) and EtOAc (5 mL) was added and the phases were separated. The aq. phase was re-extracted with EtOAc and the combined organic layers were dried over MgSO4, filtered and evaporated. Purification by preparative HPLC afforded 7 mg (16% yield) of the title compound: $^1$H NMR (500 MHz, DMSO-$d_6$) δ ppm 0.95 (m, 1 H), 1.32 (m, 5 H), 1.83 (m, 2 H), 2.08 (s, 3 H), 2.13 (s, 3 H), 2.18 (s, 3 H), 2.99 (m, 3 H), 3.20 (s, 3 H), 6.35 (s, 1 H), 6.47

(s, 2 H), 7.24 (s, 1 H), 7.65 (s, 1 H), 8.35 (d, 1 H), 8.53 (d, 1 H); MS (APCI+) m/z 427 [M+H]+.

Example 3

3-[(1r,4r)-4"-Amino-4-methoxy-5',5"-dimethyl-3'H-dispiro[cyclohexane-1,2'-indene-1',2"-imidazol]-6'-yl]-5-chlorobenzonitrile

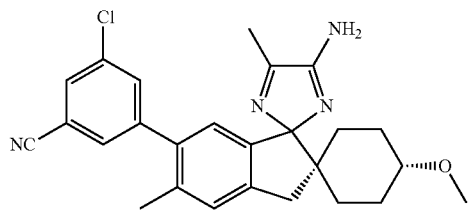

Sodium tetrachloropalladate(II) (2.3 mg, 7.69 μmol), 3-(di-tert-butylphosphonium)propane sulfonate (4.1 mg, 0.02 mmol), (1r,4r)-6'-bromo-4-methoxy-5',5"-dimethyl-3'H-dispiro[cyclohexane-1,2'-indene-1',2"-imidazol]-4"-amine (Example 1, 60 mg, 0.15 mmol), 3-chloro-5-(4,4,5,5-tetramethyl-1,3,2-dioxaborolan-2-yl)benzonitrile (61 mg, 0.23 mmol) and 2 M aq. potassium carbonate (0.231 mL, 0.46 mmol) were mixed in 1,4-dioxane (1.5 mL) and the mixture was degassed for a couple of min. by a stream of $N_2$ (g). The reaction mixture was heated at reflux for 2 h and was then allowed to cool to r.t. Water and EtOAc were added and the phases were separated. The aq. phase was extracted with EtOAc and the combined organic layers were dried over $MgSO_4$, filtered and evaporated. Purification by preparative HPLC afforded 24 mg (34% yield) of the title compound: $^1$H NMR (500 MHz, DMSO-$d_6$) δ ppm 0.94 (m, 1 H), 1.20 (m, 2 H), 1.44 (m, 3 H), 1.82 (m, 2 H), 2.13 (s, 3 H), 2.18 (s, 3 H), 2.99 (m, 3 H), 3.19 (s, 3 H), 6.37 (s, 1 H), 6.47 (s, 2 H), 7.24 (s, 1 H), 7.65 (s, 1 H), 7.71 (s, 1 H), 7.99 (s, 1 H); MS (APCI+) m/z 447 [M+H]+.

Example 4

6'-Bromo-5'-fluoro-4-methoxy-5"-methyl-3'H-dispiro[cyclohexane-1,2'-indene-1',2"-imidazol]-4"-amine

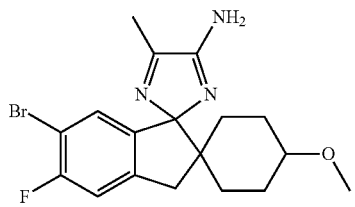 [SMILES: COC1CCC2(CC1)Cc1cc(F)c(Br)cc1C21N=C(C)C(N)=N1]

6'-Bromo-5'-fluoro-4-methoxy-5"-methyl-3'H-dispiro [cyclohexane-1,2'-indene-1',2"-imidazole]-4"(3"H)-thione (Intermediate 14, 0.500 g, 1.22 mmol) and ammonia (7 M in MeOH) (16.5 mL, 115 mmol) were mixed in a MW vial. The vial was sealed and the reaction was heated at 100° C. for 30 min in a MW reactor (fixed hold time). The mixture was concentrated and the residue was dissolved in new ammonia (7 M in MeOH) (16.5 mL, 115 mmol) and heated once more at 100° C. for 30 min in a MW reactor. 4 cycles of concentration, addition of ammonia and heating were performed in total. After evaporation of the solvent, the residue was partitioned between EtOAC and 2 M citric acid (10 mL). The phases were separated and the organic layer was re-extracted with 2 M citric acid (10 mL). The organic layer was discarded while the combined aqueous phases were basified to pH 12 by addition of 50% aq. NaOH and then extracted with EtOAc. The combined organic layers were dried over magnesium sulfate and concentrated, to give the title compound (0.354 g, 74% yield) as a diastereomer mixture in the ratio ~4:1 (established by HPLC). $^1$H NMR (500 MHz, DMSO-$d_6$, contains both isomers) δ ppm 0.88-0.99 (m, 1 H) 1.09-1.28 (m, 4 H) 1.32-1.52 (m, 3.8 H) 1.58-1.72 (m, 1 H) 1.81 (d, 2 H) 2.16 (s, 3.8 H) 2.88-3.07 (m, 3.7H) 3.12 (s, 0.8 H) 3.18 (s, 3 H) 6.60 (br. s., 2.6 H) 6.75 (d, 1.21 H) 7.32 (d, 1.26 H); MS (ES+) m/z 394, 396 [M+H]+.

Example 5

3-[(1s,4s)-4"-Amino-5'-fluoro-4-methoxy-5"-methyl-3'H-dispiro[cyclohexane-1,2'-indene-1',2"-imidazol]-6'-yl]-5-chlorobenzonitrile

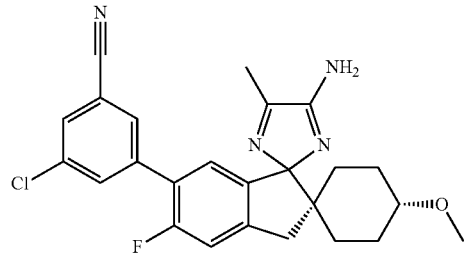

6'-Bromo-5'-fluoro-4-methoxy-5"-methyl-3'H-dispiro [cyclohexane-1,2'-indene-1',2"-imidazol]-4"-amine (Example 4, 0.133 g, 0.34 mmol), sodium tetrachloropalladate (II) (0.014 g, 0.05 mmol), 3-(di-tert-butylphosphonium) propane sulfonate (0.025 g, 0.09 mmol) and 3-chloro-5-(4,4,5,5-tetramethyl-1,3,2-dioxaborolan-2-yl)benzonitrile (0.116 g, 0.44 mmol) were weighed into a MW vial, followed by addition of 2-Me THF (4 mL) and aq. potassium carbonate (2.0 M) (0.506 mL, 1.01 mmol). The vial was closed, and the atmosphere over the reaction mixture was exchanged to argon. The vial was heated to 100° C. for 30 min. The reaction mixture was cooled to r.t., diluted with EtOAc and washed with brine. The organic layer was collected, dried over $MgSO_4$, filtered, and concentrated in vacuo. Purification of the residue by preparation HPLC afforded the title compound (0.048 g, 31% yield). $^1$H NMR (500 MHz, DMSO-$d_6$) δ ppm 1.15 (dd, J=13.08, 3.31 Hz, 2 H) 1.21-1.32 (m, 1 H) 1.39-1.57 (m, 2 H) 1.60-1.78 (m, 3 H) 2.16 (s, 3 H) 2.95-3.16 (m, 6 H) 3.30 (br. s., 1 H) 6.54 (s, 2 H) 6.70 (d, J=7.25 Hz, 1 H) 7.29 (d, J=10.72 Hz, 1 H) 7.84 (s, 1 H) 7.89 (s, 1 H) 8.03 (s, 1 H); MS (ES+) m/z 451 [M+H]+.

Example 6

Separation of the isomers of 3-[(1r,4r)-4"-amino-5'-fluoro-4-methoxy-5"-methyl-3'H-dispiro[cyclohexane-1,2'-indene-1',2"-imidazol]-6'-yl]-5-chlorobenzonitrile The enantiomers of 3-[(1r,4r)-4"-amino-5'-fluoro-4-methoxy-5"-methyl-3'H-dispiro[cyclohexane-1,2'-indene-1',2"- imidazol]-6'-yl]-5-chlorobenzonitrile (Example 5, 38 mg) were separated using a SFC Berger Multigram II preparative HPLC, with a LuxC4; 4.6*250 mm; 5 μm column, and a mobile phase consisting of 30% MeOH (containing 0.1% DEA) and 70% CO₂ at a flow rate of 50 mL/min to give:

Isomer 1

3-[(1r,1'R,4R)-4"-amino-5'-fluoro-4-methoxy-5"-methyl-3'H-dispiro[cyclohexane-1,2'-indene-1',2"-imidazol]-6'-yl]-5-chlorobenzonitrile with retention time 3.2 min (15 mg, 40% yield).

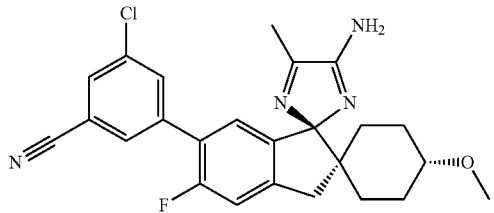

¹H NMR (500 MHz, DMSO-d₆) δ ppm 0.90-1.03 (m, 1 H) 1.10-1.31 (m, 3 H) 1.35-1.52 (m, 4 H) 1.83 (d, 2 H) 2.16 (s, 4 H) 2.89-3.13 (m, 4 H) 3.14-3.18 (m, 2 H) 3.19 (s, 3 H) 6.54 (s, 2 H) 6.71 (d, 1 H) 7.30 (d, 1 H) 7.84 (d, 1 H) 7.89 (d, 1 H) 8.03 (t, 1 H); MS (ES+) m/z 451 [M+H]⁺.

Isomer 2

3-[(1r,1'S,4S)-4"-amino-5'-fluoro-4-methoxy-5"-methyl-3'H-dispiro[cyclohexane-1,2'-indene-1',2"-imidazol]-6'-yl]-5-chlorobenzonitrile with retention time 5.8 min (15 mg, 40% yield).

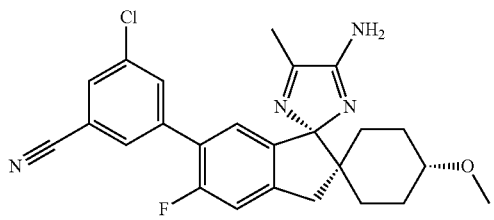 [SMILES: CO[C@H]1CC[C@]2(CC1)Cc1cc(F)c(-c3cc(Cl)cc(C#N)c3)cc1[C@]21N=C(C)C(N)=N1]

¹H NMR (500 MHz, DMSO-d₆) δ ppm 0.90-1.02 (m, 1 H) 1.09-1.30 (m, 2 H) 1.35-1.53 (m, 3 H) 1.83 (d, 2 H) 2.16 (s, 3 H) 2.89-3.13 (m, 3 H) 3.15-3.18 (m, 2 H) 3.20 (s, 3 H) 6.55 (s, 2 H) 6.72 (d, 1 H) 7.30 (d, 1 H) 7.84 (d, 1 H) 7.89 (d, 1 H) 8.04 (t, 1 H); MS (ES+) m/z 451 [M+H]⁺.

Example 7

(1r,4r)-6'-(5-Chloropyridin-3-yl)-5'-fluoro-4-methoxy-5"-methyl-3'H-dispiro[cyclohexane-1,2'-indene-1',2"-imidazol]-4"-amine

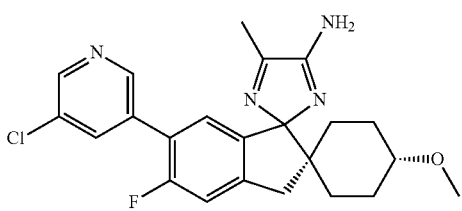

6'-Bromo-5'-fluoro-4-methoxy-5"-methyl-3'H-dispiro[cyclohexane-1,2'-indene-1',2"-imidazol]-4"-amine (Example 4, 0.052 g, 0.13 mmol), sodium tetrachloropalladate (II) (5.4 mg, 0.02 mmol), and 3-(di-tert-butylphosphonium) propane sulfonate (9.9 mg, 0.04 mmol) were weighed into a MW vial, followed by addition of 2-Me THF (3 mL) and aq. potassium carbonate (2.0 M) (0.198 mL, 0.40 mmol). The vial was closed, and the atmosphere over the reaction mixture was exchanged to argon. The vial was heated to 100° C. for 30 min. The reaction mixture was cooled to r.t., diluted with EtOAc and washed with brine. The organic layer was collected, dried over MgSO₄, filtered, and concentrated in vacuo. Purification of the residue by preparative HPLC afforded the title compound (26 mg, 46% yield). ¹H NMR (500 MHz, DMSO-d₆) δ ppm 0.90-1.02 (m, 1 H) 1.10-1.29 (m, 2 H) 1.36-1.53 (m, 3 H) 1.83 (d, 2 H) 2.16 (s, 3 H) 2.91-3.14 (m, 3 H) 3.20 (s, 3 H) 6.55 (s, 2 H) 6.72 (d, 1 H) 7.32 (d, 1 H) 8.00 (s, 1 H) 8.58 (s, 1 H) 8.61 (d, 1 H); MS (ES+) m/z 427 [M+H]⁺.

Example 8

3-[(1r,4r)-4"-Amino-5'-fluoro-4-methoxy-5"-methyl-3'H-dispiro[cyclohexane-1,2'-indene-1',2"-imidazol]-6'-yl]-5-fluorobenzonitrile

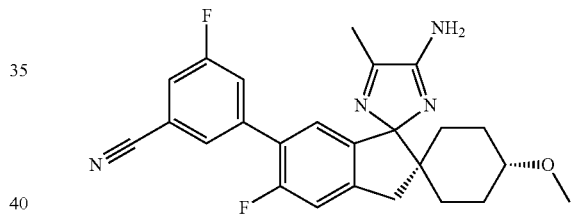

3-Cyano-5-fluorophenylboronic acid (0.043 g, 0.26 mmol), sodium tetrachloropalladate(II) (2.54 mg, 8.62 μmol) and 3-(di-tert-butylphosphonium)propane sulfonate (4.63 mg, 0.02 mmol) were put in a MW vial. (1r,4r)-6'-Bromo-5'-fluoro-4-methoxy-5"-methyl-3'H-dispiro[cyclohexane-1,2'-indene-1',2"-imidazol]-4"-amine (Example 4, 0.068 g, 0.17 mmol) dissolved in 2-Me THF (2 mL) was added followed by aq. potassium carbonate (2.0 M) (0.259 mL, 0.52 mmol) and the mixture was degassed. The mixture was then heated at 100° C. in a MW reactor for 30 min. More 3-cyano-5-fluorophenylboronic acid (0.043 g, 0.26 mmol) and 3-(di-tert-butylphosphonium)propane sulfonate (4.63 mg, 0.02 mmol) were added and heating continued for another 30 min. Water and EtOAc were added and the phases were separated. The aqueous phase was re-extracted with EtOAc and the combined organic layers were dried over MgSO₄ and concentrated. The residue was purified by preparative chromatography, followed by silica gel chromatography purification using 3% (0.1 M NH₃ in MeOH) in EtOAc as eluent to give the title compound (38 mg, 50% yield). ¹H NMR (500 MHz, DMSO-d₆) δ 0.90-1.01 (m, 1 H), 1.22 (s, 2 H), 1.44 (br. s., 3 H), 1.83 (d, J=9.46 Hz, 2 H), 2.16 (s, 3 H), 2.91-2.98 (m, 1 H), 2.98-3.13 (m, 2 H), 3.20 (s, 3 H), 6.55 (s, 2 H), 6.72 (d, J=7.57 Hz, 1 H), 7.30 (d, J=10.72 Hz, 1 H), 7.69 (d, J=9.77 Hz, 1 H), 7.77 (s, 1 H), 7.85 (d, J=8.51 Hz, 1 H); MS (ES+) m/z 435 [M+H]⁺.

Example 9

Separation of the isomers of 3-[(1r,4r)-4"-amino-5'-fluoro-4-methoxy-5"-methyl-3'H-dispiro[cyclohexane-1,2'-indene-1',2"-imidazol]-6'-yl]-5-fluorobenzonitrile The enantiomers of 3-[(1r,4r)-4"-amino-5'-fluoro-4-methoxy-5"-methyl-3'H-dispiro[cyclohexane-1,2'-indene-1',2"-imidazol]-6'-yl]-5-fluorobenzonitrile (Example 8, 0.027 g) were separated using a SFC Berger Multigram II preparative HPLC, with a LuxC4; 20*250 mm; 5 μm column, and a mobile phase consisting of 30% MeOH (containing 0.1% DEA) and 70% $CO_2$ at a flow rate of 50 mL/min to give:

Isomer 1

3-[(1r,1'R,4R)-4"-amino-5'-fluoro-4-methoxy-5"-methyl-3'H-dispiro[cyclohexane-1,2'-indene-1',2"-imidazol]-6'-yl]-5-fluorobenzonitrile with retention time 4.5 min (5 mg, 17% yield).

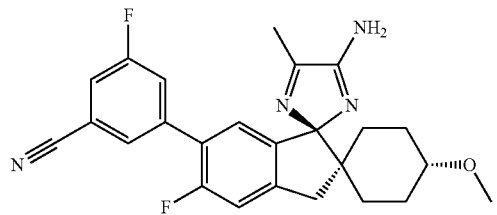 [SMILES: CO[C@H]1CC[C@]2(CC1)Cc1cc(F)c(-c3cc(F)cc(C#N)c3)cc1[C@@]21N=C(C)C(N)=N1]

$^1$H NMR (500 MHz, DMSO-$d_6$) δ ppm 0.95 (m, 1 H) 1.20 (m, 2 H) 1.43 (m, 2 H) 1.84 (m, 1 H) 2.16 (s, 2 H) 2.94 (m, 1 H) 3.05 (m, 2 H) 3.20 (s, 2 H) 6.53 (m, 1 H) 6.72 (m, 1 H) 7.30 (m, 1 H) 7.68 (m, 1 H) 7.77 (m, 1 H) 7.85 (m, 1 H); MS (APCI+) m/z 435 [M+H]$^+$.

Isomer 2

3-[(1r,1'S,4S)-4"-amino-5'-fluoro-4-methoxy-5"-methyl-3'H-dispiro[cyclohexane-1,2'-indene-1',2"-imidazol]-6'-yl]-5-fluorobenzonitrile with retention time 10.1 min (12 mg, 46% yield).

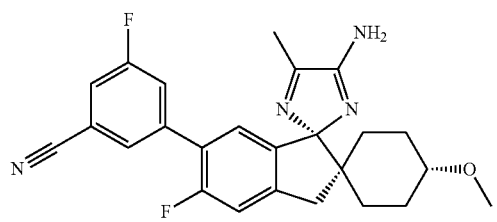 [SMILES: CO[C@H]1CC[C@]2(CC1)Cc1cc(F)c(-c3cc(F)cc(C#N)c3)cc1[C@]21N=C(C)C(N)=N1]

$^1$H NMR (500 MHz, DMSO-$d_6$) δ ppm 0.95 (m, 1 H) 1.22 (m, 3 H) 1.44 (br. s., 3 H) 1.83 (d, 2 H) 2.16 (s, 3 H) 2.93 (m, 1 H) 3.07 (m, 2 H) 3.20 (s, 3 H) 6.55 (s, 2 H) 6.72 (d, 1 H) 7.30 (d, 1 H) 7.69 (m, 1 H) 7.77 (d, 1 H) 7.85 (m, 1 H); MS (APCI+) m/z 435 [M+H]$^+$.

Example 10

5'-Fluoro-6'-(3-fluoropropoxy)-4-methoxy-5"-methyl-3'H-dispiro[cyclohexane-1,2'-indene-1',2"-imidazol]-4"-amine

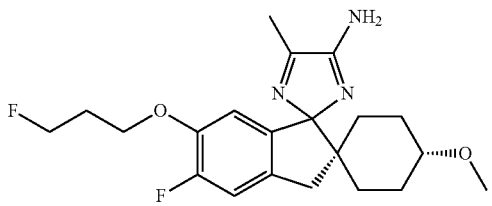

Methanolic ammonia (7 M, 1.89 mL, 13.2 mmol) and toluene (2 mL) was added to di-tert-butyl [5'-fluoro-6'-(3-fluoropropoxy)-4-methoxy-5"-methyl-3'H-dispiro[cyclohexane-1,2'-indene-1',2"-imidazol]-4"-yl]imidodicarbonate (Intermediate 16, 260 mg, 0.44 mmol). The mixture was transferred to a MW vial which was capped and heated to 85° C. for a week. The mixture was concentrated and partitioned between EtOAc and 2 M citric acid. The phases were separated and the organic phase was discarded. The aqueous phase was basified by addition of 50% aq. NaOH solution to pH 12 and then extracted with EtOAc. The combined organic phases were treated with charcoal, filtered through diatomaceous earth and concentrated. Purification of the residue by preparative HPLC afforded the title compound (17 mg, 10% yield).
$^1$H NMR (500 MHz, DMSO-$d_6$) δ ppm 0.83-0.95 (m, 1 H) 1.07-1.26 (m, 2 H) 1.33-1.49 (m, 3 H) 1.76-1.85 (m, 2 H) 1.97-2.11 (m, 2 H) 2.13-2.19 (m, 3 H) 2.82-2.99 (m, 3 H) 3.18 (s, 3 H) 3.90-4.01 (m, 2 H) 4.51 (t, 1 H) 4.61 (t, 1 H) 6.26 (d, 1 H) 6.53 (s, 2 H) 7.13 (d, 1 H); MS (ES+) m/z 392 [M+H]$^+$.

Biological Assays

The level of activity of the compounds was tested using the following methods:

TR-FRET Assay

The β-secretase enzyme used in the TR-FRET is prepared as follows:

The cDNA for the soluble part of the human β-Secretase (AA 1-AA 460) was cloned using the ASP2-Fc10-1-IRES-GFP-neoK mammalian expression vector. The gene was fused to the Fc domain of IgG1 (affinity tag) and stably cloned into HEK 293 cells. Purified sBACE-Fc was stored in −80° C. in 50 mM Glycine pH 2.5, adjusted to pH 7.4 with 1 M Tris and had a purity of 40%.

The enzyme (truncated form) was diluted to 6 μg/mL (stock 1.3 mg/mL) and the TruPoint BACE1 Substrate to 200 nM (stock 120 μM) in reaction buffer (NaAcetate, chaps, triton x-100, EDTA pH4.5). Enzyme and compound in dimethylsulphoxide (final DMSO concentration 5%) was mixed and pre-incubated for 10 minutes at RT. Substrate was then added and the reaction was incubated for 15 minutes at RT. The reaction was stopped with the addition of 0.35 vol Stop solution (NaAcetate, pH 9). The fluorescence of the product was measured on a Victor II plate reader with excitation wavelengths of 340-485 nm and emission wavelengths of 590-615 nm. The final concentration of the enzyme was 2.7 μg/ml; the final concentration of substrate was 100 nM (Km of ~250 nM). The dimethylsulphoxide control, instead of test compound, defined the 100% activity level and 0% activity was defined by wells lacking enzyme (replaced with reaction buffer) or by a saturating dose of a known inhibitor, 2-amino-6-[3-(3-methoxyphenyl)phenyl]-3,6-dimethyl-5H-pyrimidin-4-one. A control inhibitor was also used in dose response assays and had an IC50 of ~150 nM.

Diluted TR-FRET Assay

Compounds with a high affinity were further tested in a diluted TR-FRET assay, conditions as described above for the TR-FRET assay, but with 50 times less enzyme and a 6.5 h long reaction time at r.t. in the dark.

sAPPβ Release Assay

SH-SY5Y cells were cultured in DMEM/F-12 with Glutamax, 10% FCS and 1% non-essential amino acids and cryopreserved and stored at −140° C. at a concentration of 7.5–9.5×10⁶ cells per vial. Thaw cells and seed at a conc. of around 10000 cells/well in DMEM/F-12 with Glutamax, 10% FCS and 1% non-essential amino acids to a 384-well tissue culture treated plate, 100 µL cell susp/well. The cell plates were then incubated for 7-24 h at 37° C., 5% CO₂. The cell medium was removed, followed by addition of 30 µL compound diluted in DMEM/F-12 with Glutamax, 10% FCS, 1% non-essential amino acids and 1% PeSt to a final conc. of 1% DMSO. The compounds were incubated with the cells for 17 h (overnight) at 37° C., 5% CO₂. Meso Scale Discovery (MSD) plates were used for the detection of sAPPβ release. MSD sAPPβ plates were blocked in 1% BSA in Tris wash buffer (40 µL/well) for 1 h on shake at r.t. and washed 1 time in Tris wash buffer (40 µL/well). 20 µL of medium was transferred to the pre-blocked and washed MSD sAPPβ microplates, and the cell plates were further used in an ATP assay to measure cytotoxicity. The MSD plates were incubated with shaking at r.t. for 2 h and the media discarded. 10 µL detection antibody was added (1 nM) per well followed by incubation with shaking at r.t. for 2 h and then discarded. 40 µL Read Buffer was added per well and the plates were read in a SECTOR Imager.

ATP Assay

As indicated in the sAPPβ release assay, after transferring 20 µL medium from the cell plates for sAPPβ detection, the plates were used to analyse cytotoxicity using the ViaLight™ Plus cell proliferation/cytotoxicity kit from Cambrex Bio-Science that measures total cellular ATP. The assay was performed according to the manufacture's protocol. Briefly, 10 µL cell lysis reagent was added per well. The plates were incubated at r.t. for 10 min. Two min after addition of 25 µL reconstituted ViaLight™ Plus ATP reagent, the luminescence was measured. Tox threshold is a signal below 75% of the control.

Results

Typical $IC_{50}$ values for the compounds of the present invention are in the range of about 0.1 to about 100,000 nM. Biological data on particular example compounds is given below in Table 1.

TABLE 1

| Example | $IC_{50}$ in TR-FRET assay (nM) | $IC_{50}$ in sAPPβ release assay (nM) | Example | $IC_{50}$ in TR-FRET assay (nM) | $IC_{50}$ in sAPPβ release assay (nM) |
|---|---|---|---|---|---|
| 1 | 1659 | ND | 2 | 15$^a$ | 17 |
| 3 | 24$^a$ | 12 | 4 | 516 | 176 |
| 5 | 23 | 1.7 | 6 Isomer 1 | 2.4$^a$ | 0.8 |

TABLE 1-continued

| Example | $IC_{50}$ in TR-FRET assay (nM) | $IC_{50}$ in sAPPβ release assay (nM) | Example | $IC_{50}$ in TR-FRET assay (nM) | $IC_{50}$ in sAPPβ release assay (nM) |
|---|---|---|---|---|---|
| 6 Isomer 2 | >4300 | 986 | 7 | 36 | 3.0 |
| 8 | 23 | 4.8 | 9 Isomer 1 | 13$^a$ | 7.4 |
| 9 Isomer 2 | >5000 | ND | 10 | 39 | ND |

$^a$$IC_{50}$ from the diluted FRET assay.

The invention claimed is:

1. A compound according to formula (I):

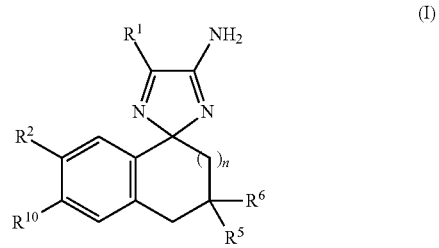

wherein
n is 0 or 1;
$R^1$ is $C_{1-6}$alkyl or $C_{1-6}$haloalkyl;
$R^2$ is hydrogen, $C_{0-6}$alkylaryl, $C_{0-6}$alkylheteroaryl, $C_{2-6}$alkynyl, $C_{2-6}$alkenyl, $C_{1-6}$alkyl, halogen, cyano, $C_{1-6}$haloalkyl, NHC(O)$R^9$ or O$R^8$, wherein said $C_{0-6}$alkylaryl, $C_{0-6}$alkylheteroaryl, $C_{2-6}$alkynyl, $C_{2-6}$alkenyl, $C_{1-6}$alkyl or $C_{1-6}$haloalkyl is optionally substituted with one to three $R^7$;
$R^5$ and $R^6$ are independently hydrogen, heterocyclyl, $C_{3-6}$cycloalkyl, aryl, heteroaryl or $C_{1-6}$alkyl, wherein said heterocyclyl, $C_{3-6}$cycloalkyl, aryl, heteroaryl or $C_{1-6}$alkyl is optionally substituted with one or two substituents independently selected from halogen, $C_{1-6}$alkyl, $C_{1-6}$haloalkyl, cyano or O$R^8$;
or $R^5$ and $R^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, $C_{1-6}$alkyl, $C_{1-6}$haloalkyl, cyano, or O$R^8$; and ring B is optionally fused with an aryl or heteroaryl to form a bi- or polycyclic system;
$R^7$ is independently $C_{1-6}$alkyl, halogen, cyano, $C_{0-6}$alkyl$C_{3-6}$cycloalkyl, $C_{1-6}$haloalkyl, O$C_{1-6}$alkyl, O$C_{1-6}$haloalkyl, $C_{2-6}$alkynyl or $C_{2-6}$alkenyl, wherein said $C_{1-6}$alkyl, $C_{0-6}$alkyl $C_{3-6}$cycloalkyl, $C_{1-6}$haloalkyl, O$C_{1-6}$alkyl, O$C_{1-6}$haloalkyl, $C_{2-6}$alkynyl or $C_{2-6}$alkenyl is optionally substituted with 1-3 substituents independently selected from halogen, cyano, $C_{1-6}$alkyl, $C_{1-6}$haloalkyl, O$C_{1-6}$alkyl, $C_{3-6}$ cycloalkyl, $C_{3-6}$halocycloalkyl, and O$C_{1-6}$haloalkyl;
$R^8$ is independently hydrogen, $C_{1-6}$alkyl, $C_{2-6}$alkynyl, $C_{1-6}$haloalkyl, aryl or heteroaryl, wherein said $C_{1-6}$alkyl, $C_{1-6}$haloalkyl, aryl or heteroaryl is optionally substituted with a group selected from halogen, cyano, $C_{3-6}$cycloalkyl, $C_{3-6}$halocycloalkyl, O$C_{1-6}$alkyl and $C_{1-6}$alkyl;

R⁹ is a heteroaryl, wherein said heteroaryl is optionally substituted with halogen, cyano, OR⁸, $C_{1-6}$haloalkyl or $C_{1-6}$alkyl;

R¹⁰ is halogen or methyl;

as a free base or a pharmaceutically acceptable salt thereof.

2. A compound according to claim 1, or a pharmaceutically acceptable salt thereof, wherein R¹ is $C_{1-3}$alkyl.

3. A compound according to claim 2, or a pharmaceutically acceptable salt thereof, wherein R¹ is methyl or ethyl.

4. A compound according to claim 1, or a pharmaceutically acceptable salt thereof, wherein R² is aryl, heteroaryl, $C_{2-6}$alkynyl, halogen, NHC(O)R⁹ or OR⁸, wherein said aryl, heteroaryl, or $C_{2-6}$alkynyl is optionally substituted with one to three R⁷.

5. A compound according to claim 1, or a pharmaceutically acceptable salt thereof, wherein R⁵ and R⁶ are independently hydrogen, $C_{3-6}$cycloalkyl or heterocyclyl wherein said $C_{3-6}$cycloalkyl or heterocyclyl is optionally substituted with one or two substituents independently selected from $C_{1-6}$alkyl or OR⁸.

6. A compound according to claim 1, or a pharmaceutically acceptable salt thereof, wherein R⁵ and R⁶ together with the carbon to which they are attached, form a ring B, which is a 3-6 membered cycloalkyl or heterocyclyl monocyclic ring; and wherein ring B is optionally substituted by one or two substituents independently selected from oxo, halogen, $C_{1-6}$alkyl or OR⁸.

7. A compound according to claim 1, or a pharmaceutically acceptable salt thereof, wherein R⁵ and R⁶ together with the carbon to which they are attached form a cyclohexyl ring, which is substituted with OR⁸.

8. A compound according to claim 1, or a pharmaceutically acceptable salt thereof, wherein R⁷ is independently $C_{1-6}$alkyl, halogen, cyano, $C_{0-6}$alkyl$C_{3-6}$cycloalkyl, $C_{1-6}$haloalkyl, OC$_{1-6}$alkyl or $C_{2-6}$alkynyl, wherein said $C_{1-6}$alkyl, $C_{0-6}$alkyl$C_{3-6}$cycloalkyl, $C_{1-6}$haloalkyl, OC$_{1-6}$alkyl or $C_{2-6}$alkynyl is optionally substituted with 1-3 substituents independently selected from halogen, cyano, $C_{1-6}$alkyl, $C_{1-6}$haloalkyl, OC$_{1-6}$alkyl, $C_{3-6}$cycloalkyl, $C_{3-6}$halocycloalkyl and OC$_{1-6}$haloalkyl.

9. A compound according to claim 1, or a pharmaceutically acceptable salt thereof, wherein R⁷ is independently halogen, cyano or $C_{2-6}$alkynyl, wherein said $C_{2-6}$alkynyl is optionally substituted with 1-3 substituents independently selected from $C_{1-6}$alkyl, $C_{3-6}$cycloalkyl, $C_{3-6}$halocycloalkyl or $C_{1-6}$haloalkyl.

10. A compound according to claim 1, or a pharmaceutically acceptable salt thereof, wherein R⁸ is independently hydrogen, $C_{1-6}$alkyl or $C_{1-6}$haloalkyl.

11. A compound according to claim 1, or a pharmaceutically acceptable salt thereof, wherein R⁹ is heteroaryl, wherein said heteroaryl is optionally substituted with halogen, cyano, OR⁸, $C_{1-6}$haloalkyl or $C_{1-6}$ alkyl.

12. A compound according to claim 1, or a pharmaceutically acceptable salt thereof, wherein n is 0 or 1;

R¹ is $C_{1-6}$alkyl;

R² is aryl, heteroaryl, $C_{2-6}$alkynyl, halogen, NHC(O)R⁹ or OR⁸; wherein said aryl, heteroaryl or $C_{2-6}$alkynyl is optionally substituted with one to three R⁷;

R⁵ and R⁶ are independently hydrogen, $C_{3-6}$cycloalkyl, or heterocyclyl, wherein said $C_{3-6}$cycloalkyl or heterocyclyl is optionally substituted with one or two substituents independently selected from halogen, $C_{1-6}$alkyl, $C_{1-6}$haloalkyl or OR⁸;

or R⁵ and R⁶ together with the carbon to which they are attached, form a ring B, which is a 3-6 membered cycloalkyl or heterocyclyl monocyclic ring; and wherein ring B is optionally substituted by one or two substituents independently selected from oxo, halogen, $C_{1-6}$alkyl or OR⁸;

R⁷ is independently $C_{1-6}$alkyl, halogen, cyano, $C_{0-6}$alkyl$C_{3-6}$cycloalkyl, $C_{1-6}$haloalkyl, OC$_{1-6}$alkyl or $C_{2-6}$alkynyl, wherein said $C_{1-6}$alkyl, $C_{0-6}$alkyl$C_{3-6}$cycloalkyl, $C_{1-6}$haloalkyl, OC$_{1-6}$alkyl or $C_{2-6}$alkynyl is optionally substituted with 1-3 substituents independently selected from halogen, cyano, $C_{1-6}$alkyl, $C_{1-6}$haloalkyl, OC$_{1-6}$alkyl and OC$_{1-6}$haloalkyl;

R⁸ is independently $C_{1-6}$alkyl or $C_{1-6}$haloalkyl, wherein said $C_{1-6}$alkyl or $C_{1-6}$haloalkyl is optionally substituted with a group selected from halogen, $C_{3-6}$cycloalkyl, $C_{3-6}$halocycloalkyl, or $C_{1-6}$alkyl;

R⁹ is heteroaryl, wherein said heteroaryl is optionally substituted with halogen, cyano, OR⁸, $C_{1-6}$haloalkyl or $C_{1-6}$alkyl; and R¹⁰ is halogen or methyl.

13. A compound according to claim 1, or a pharmaceutically acceptable salt thereof, wherein n is 0 or 1;

R¹ is $C_{1-3}$alkyl;

R² is aryl, heteroaryl, $C_{2-6}$alkynyl, halogen, NHC(O)R⁹ or OR⁸, wherein said aryl, heteroaryl or $C_{2-6}$alkynyl is optionally substituted with one to three R⁷;

R⁵ and R⁶ are independently hydrogen, $C_{3-6}$cycloalkyl or heterocyclyl, wherein said $C_{3-6}$cycloalkyl or heterocyclyl is optionally substituted with one or two substituents independently selected from $C_{1-6}$alkyl or OR⁸;

or R⁵ and R⁶ together with the carbon to which they are attached, form a ring B, which is a 3-6 membered cycloalkyl or heterocyclyl monocyclic ring; and wherein ring B is optionally substituted by one or two substituents independently selected from oxo, halogen, $C_{1-6}$alkyl or OR⁸;

R⁷ is independently $C_{1-6}$alkyl, halogen, cyano, $C_{0-6}$alkyl$C_{3-6}$cycloalkyl, $C_{1-6}$haloalkyl, OC$_{1-6}$alkyl or $C_{2-6}$alkynyl, wherein said $C_{1-6}$alkyl, $C_{0-6}$alkyl$C_{3-6}$cycloalkyl, $C_{1-6}$haloalkyl, OC$_{1-6}$alkyl or $C_{2-6}$alkynyl is optionally substituted with 1-3 substituents independently selected from halogen, cyano, $C_{1-6}$alkyl, $C_{1-6}$haloalkyl, OC$_{1-6}$alkyl and OC$_{1-6}$haloalkyl;

R⁸ is independently $C_{1-6}$alkyl or $C_{1-6}$haloalkyl, wherein said $C_{1-6}$alkyl or $C_{1-6}$haloalkyl is optionally substituted with a group selected from halogen or $C_{1-6}$alkyl;

R⁹ is heteroaryl, wherein said heteroaryl is optionally substituted with halogen, cyano, OR⁸, $C_{1-6}$haloalkyl or $C_{1-6}$ alkyl; and R¹⁰ is halogen or methyl.

14. A compound according to claim 1, selected from the group consisting of:

(1r,4r)-6'-Bromo-4-methoxy-5',5''-dimethyl-3'H-dispiro[cyclohexane-1,2'-indene-1',2''-imidazol]-4''-amine;

(1r,4r)-4-Methoxy-5',5''-dimethyl-6'-[5-(prop-1-yn-l-yl)pyridin-3-yl]-3'H-dispiro[cyclohexane-1,2'-indene-1',2''-imidazol]-4''-amine;

3-[(1r,4r)-4''-Amino-4-methoxy-5',5''-dimethyl-3'H-dispiro[cyclohexane-1,2'-indene-1',2''-imidazol]-6'-yl]-5-chlorobenzonitrile;

6'-Bromo-5'-fluoro-4-methoxy-5''-methyl-3'H-dispiro[cyclohexane-1,2'-indene-1',2''-imidazol]-4''-amine;

3-[(1s,4s)-4"-Amino-5'-fluoro-4-methoxy-5"-methyl-3'H-dispiro[cyclohexane-1,2'-indene-1',2"-imidazol]-6'-yl]-5-chlorobenzonitrile;

3-[(1r,1'R,4R)-4"-amino-5'-fluoro-4-methoxy-5"-methyl-3'H-dispiro[cyclohexane-1,2'-indene-1',2"-imidazol]-6'-yl]-5-chlorobenzonitrile;

3-[(1r,1'S,4S)-4"-amino-5'-fluoro-4-methoxy-5"-methyl-3'H-dispiro[cyclohexane-1,2'-indene-1',2"-imidazol]-6'-yl]-5-chlorobenzonitrile;

(1r,4r)-6'-(5-Chloropyridin-3-yl)-5'-fluoro-4-methoxy-5"-methyl-3'H-dispiro[cyclohexane-1,2'-indene-1',2"-imidazol]-4"-amine;

3-[(1r,4r)-4"-Amino-5'-fluoro-4-methoxy-5"-methyl-3'H-dispiro[cyclohexane-1,2'-indene-1',2"-imidazol]-6'-yl]-5-fluorobenzonitrile;

3-[(1r,1'R,4R)-4"-amino-5'-fluoro-4-methoxy-5"-methyl-3'H-dispiro[cyclohexane-1,2'-indene-1',2"-imidazol]-6'-yl]-5-fluorobenzonitrile;

3-[(1r,1'S,4S)-4"-amino-5'-fluoro-4-methoxy-5"-methyl-3'H-dispiro[cyclohexane-1,2'-indene-1',2"-imidazol]-6'-yl]-5-fluorobenzonitrile; and 5'-Fluoro-6'-(3-fluoropropoxy)-4-methoxy-5"-methyl-3'H-dispiro[cyclohexane-1,2'-indene-1',2"-imidazol]-4"-amine;

or a pharmaceutically acceptable salt of any foregoing compound.

15. The compound or pharmaceutically acceptable salt thereof according to claim 1, wherein said compound is 3-[(1r,1'R,4R)-4"-amino-5'-fluoro-4-methoxy-5"-methyl-3'H-dispiro[cyclohexane-1,2'-indene-1',2"-imidazol]-6'-yl]-5-chlorobenzonitrile :

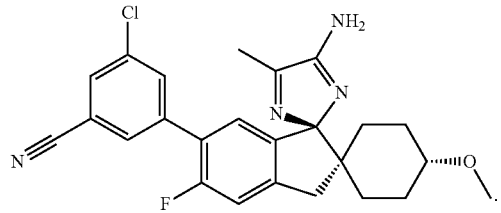 [SMILES: CO[C@H]1CC[C@]2(CC1)Cc1cc(F)c(-c3cc(Cl)cc(C#N)c3)cc1[C@@]21N=C(C)C(N)=N1]

16. A pharmaceutical composition comprising as active ingredient a therapeutically effective amount of a compound according to any one of claims 1, 14 and 15, or a pharmaceutically acceptable salt thereof, in association with at least one pharmaceutically acceptable excipient, carrier or diluent.

17. A method of treating Alzheimer's Disease in a patient in need thereof, comprising administering to said patient a therapeutically effective amount of a compound according to any one of claims 1, 14 and 15, or a pharmaceutically acceptable salt thereof.

18. A method of treating an Aβ-related pathology in a patient in need thereof, comprising administering to said patient a therapeutically effective amount of a compound according to any one of claims 1, 14 and 15, or a pharmaceutically acceptable salt thereof, and at least one cognitive enhancing agent, memory enhancing agent, or cholinesterase inhibitor, wherein said Aβ-related pathology is Alzheimer's Disease.

* * * * *